(12) United States Patent
West et al.

(10) Patent No.: US 7,071,299 B2
(45) Date of Patent: Jul. 4, 2006

(54) PEPTIDE AND POLYPEPTIDE INHIBITORS OF COMPLEMENT C1S

(75) Inventors: Robert R. West, Seattle, WA (US); Paul O. Sheppard, Granite Falls, WA (US); Brian A. Fox, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 458 days.

(21) Appl. No.: 09/883,727

(22) Filed: Jun. 18, 2001

(65) Prior Publication Data

US 2002/0102256 A1    Aug. 1, 2002

Related U.S. Application Data

(60) Provisional application No. 60/212,998, filed on Jun. 21, 2000.

(51) Int. Cl.
*C07K 7/06* (2006.01)
*C07K 7/08* (2006.01)
*C07K 14/435* (2006.01)

(52) U.S. Cl. .................. 530/324; 530/325; 530/326; 530/327; 530/328; 530/329; 530/330

(58) Field of Classification Search .............. 530/325, 530/324, 326, 327, 328, 329, 330; 424/184.1, 424/485.1, 278.1
See application file for complete search history.

*Primary Examiner*—Christina Chan
*Assistant Examiner*—F. Pierre VanderVegt
(74) *Attorney, Agent, or Firm*—Phillip B. C. Jones; Michelle L. Lewis

(57) ABSTRACT

The complement system plays an important role in providing resistance to infections and in the pathogenesis of tissue injury. Yet an inappropriate activation of complement can result in a variety of disorders. The present invention provides C1s catalytic site-directed moieties, C1s exosite binding moieties, and bivalent polypeptide inhibitors comprising such moieties, which can be used to treat conditions characterized by inappropriate complement activation.

3 Claims, No Drawings

US 7,071,299 B2

PEPTIDE AND POLYPEPTIDE INHIBITORS OF COMPLEMENT C1S

CROSS-REFERENCE TO RELATED APPLICATIONS

This application claims the benefit of U.S. Provisional application No. 60/212,998 (filed Jun. 21, 2000), the contents of which are incorporated by reference.

TECHNICAL FIELD

The present invention relates generally to new peptides and polypeptides, which inhibit complement C1s.

BACKGROUND OF THE INVENTION

The complement system is considered an ancient part of the immune system, which serves to discriminate self and non-self (see, for example, Rother et al. (Eds.), *The Complement System, Second Edition* (Springer-Verlag 1998), Morely and Walport, *The Complement Factsbook* (Academic Press 1999), and Morgan (Ed.), *Complement Methods and Protocols* (Humana Press, Inc. 2000)). Although the complement system plays an important role in providing resistance to infections, an inappropriate activation of complement can result in a variety of disorders.

There are two main pathways for complement activation, which are known as the classical and alternative pathways. Both pathways comprise a cascade of enzyme activation, which leads to the production of a terminal membrane attack complex that targets immune complexes or microorganisms. The alternative pathway is activated by the chance binding of C3b with the surface of a microorganism. The classical pathway is the principal antibody-directed mechanism for the activation of complement. C1, the first enzyme complex in the classical pathway, is a pentamolecular complex consisting of a single C1q molecule, and two C1r and C1s molecules. In the classical pathway, an antibody binds with C1q, which causes the activation of the C1r molecules. These activated proteins then cleave the C1s molecules to form active C1s serine proteases, which act on the next two components of the classical complement pathway, C4 and C2. Cleaved portions of these complement proteins, known as C4b and C2a, then form C3 convertase, which goes on to cleave the next component in the cascade, C3. Thus, C1s plays a key role, because one C1s molecule can generate multiple C4b molecules, which have an amplification effect on the system.

Molecules that inhibit complement may be beneficial for treatment of diseases in which complement activation has been shown to occur, such as adult respiratory distress syndrome, ischemia-reperfusion injury (myocardial infarct, stroke, skeletal muscle, lung inflammation), hyperacute rejection (transplantation), sepsis, cardiopulmonary bypass, burns, wound healing, asthma, restenosis, multiple organ dysfunction syndrome, trauma, hemorrhagic shock, Guillain-Barre syndrome, paroxysmal nocturnal hemoglobinuria, glomerulonephritis, systemic lupus erythematosus, rheumatoid arthritis, infertility, Alzheimer's disease, organ rejection, myasthenia gravis, multiple sclerosis, platelet storage, serum sickness, various hemolytic anemias, and hemodialysis See, for example, Vogt, *Trends Pharm. Sci.* 6:114 (1985), and Makrides, *Pharm. Rev.* 50:59 (1998).

Many different types of compounds have been found to be inhibitors of classical complement, including diamines, amino acids and their derivatives, polynucleotides, polyanions, pyridinium sulphonylfluorides and phenothiazines (see, for example, Ashghar, *Pharmac. Rev.* 36:223 (1984)). Peptide inhibitors are exemplified by amino acid sequences that mimic the C1 fixing sequences of IgG, glutathione, and leupeptin (see, for example, Boackle et al., *Nature* 282:742 (1979); Takada et al., *Immunology* 34:509 (1979)). A tripeptide based on C-terminal sequences of C3a and C5a has been shown to be a substrate for C4b2a, CVFBb and C1s, while substrate-like inhibitors of C3 convertase have also been prepared (see, for example, Andreatta et al., *In Enzyme Inhibitors*, Brodbeck (Ed.), pages 261–272 (1981); Caporale et al., *J. Immun.* 126:1963 (1981)).

Few compounds have been found to inhibit the alternative pathway. Complestatin, a microbial product believed to bind to factor B is one example of such an inhibitory compound (Kaneko et al., *J. Immun.* 124:1194 (1980)). Many inhibitors described above require relatively high concentrations, and lack specificity.

Protein inhibitors of complement have been described more recently, and include: soluble complement receptor (sCRl), a humanized monoclonal antibody to C5, and BD001, a recently described protein derived from a leech, which inhibits C1s (Liszewski and Atkinson, *Exp Opin, Invest. Drugs* 7:323 (1998); Seale and Finney, International Publication No. WO99/36439). Seale and Finney reported that BD001 has the following amino acid sequence:

```
                                        (SEQ ID NO:1)
AKKKLPKCQK QEDCGSWDLK CNNVTKKCEC RNQVCGRGCP

KERYQRDKYG CRKCLCKGCD GFKCRLGCTY GFKTDKKGCE

AFCTCNTKET ACVNIWCTDP YKCNPESGRC EDPNEEYEYD YE
```

The discovery of new C1s-inhibitory peptides and polypeptides fulfills a need in the art by providing new compositions useful in diagnosis and therapy. The present invention provides such polypeptides for these and other uses that should be apparent to those skilled in the art from the teachings herein.

BRIEF SUMMARY OF THE INVENTION

The present invention provides novel peptides and polypeptides that can inhibit the complement system. The present invention also provides methods of producing these peptides and polypeptides.

DESCRIPTION OF THE INVENTION

1. Overview

BD001, a leech protein that inhibits C1s and factor XII activation, was produced in two separate expression systems: baculovirus and *Pichia methanolica*. The baculovirus system produced a protein that is virtually identical to the native inhibitory protein isolated from the salivary complexes of the leech. That is, mass spectroscopy and N-terminal sequencing indicated that the baculorivus-derived material had the correct stop and start sites, N-glycosylation at the expected position, and tyrosine sulfation at the C-terminus on three tyrosine residues. Moreover, bioassays of this expressed material in an isolated enzymatic assay of C1s showed equivalence with the native leech material.

In contrast, the protein expressed in *Pichia methanolica* lacked the tyrosine sulfation at the C-terminus, and N-glycosylation. In addition, a portion of *Pichia*-produced BD001 molecules were truncated at the C-terminus. This *Pichia* material was found to be about 10 fold less active in bioassays, compared with the baculorivus-expressed material. Computer modeling of C1s and other serine proteases indicated that alterations in the C-terminus of BD001 could lead to diminished binding with the exosite region of C1s. This result is consistent with the decreased activity of BD001 that contained variations in the C-terminus.

Further sequence analyses revealed that complement protein C4, which is the endogenous substrate for C1s, includes a region that has a string of anionic residues with three tyrosine residues in a similar arrangement to the amino acid sequence of BD001. In addition, studies have shown that these three tyrosine residues of C4 must be sulfated in order for this molecule to have activity (Hortin et al., *J. Biol. Chem.* 261:1786 (1986); Hortin et al., *Proc. Nat'l Acad. Sci. USA*. 86:1338 (1989)). Studies described herein substantiate the importance of tyrosine sulfation for BD001 activity.

Without being bound by theory, these collective observations indicate that the C-terminal portion of BD001 mimics a portion of C4 to confer specificity of binding of BD001 for C1s. Accordingly, small peptide or peptidomimetic inhibitors of C1s can be devised, which are based upon the BD001 sequence.

As described herein, the present invention provides complement C1s inhibitors useful as therapeutic agents. These inhibitory peptides and polypeptides are also useful as preservatives in blood samples. In addition, peptides and polypeptides described herein can be used in affinity purification procedures to isolate C1s.

In particular, the present invention provides polypeptides that inhibit complement C1s, wherein the polypeptides are characterized by the formula: "P-N-[DE](2)-[YX$_1$X$_2$X$_3$]-[DE](1,2)-[YX$_1$X$_2$X$_3$]-[DE]-[YX$_1$X$_2$X$_3$]-[DE](1,2)," where amino acid residues in square brackets indicate acceptable amino acids, numbers in parentheses indicate the number of amino acid residues, "X$_1$" represents Phe-(p-CH$_2$)SO$_3$H, "X$_2$" represents sulfated tyrosine, and "X$_3$" represents 2-sulfotyrosine (SEQ ID NO: 127). Suitable polypeptides include polypeptides characterized by the formula: "P-N-[DE](2)-[YX$_1$X$_2$X$_3$]-[DE](1,2)-[YX$_1$X$_2$X$_3$]-[DE]-[YX$_1$X$_2$X$_3$]-[DE]" (SEQ ID NO:129), the formula: "P-N-E-E-[YX$_1$X$_2$X$_3$]-E-[YX$_1$X$_2$X$_3$]-E-[YX$_1$X$_2$X$_3$]-E" (SEQ ID NO:130), or by the amino acid sequence:

"PNEEY EYEYE"        (SEQ ID NO:125).

The present invention also proves polypeptides that inhibit complement C1s, wherein the polypeptide comprise an amino acid sequence that is characterized by the formula: "[AP]-N-[DE](2)-[X$_1$X$_2$X$_3$]-[DE](2)-[X$_1$X$_2$X$_3$]-[DE]-[X$_1$X$_2$X$_3$]-[DE](1,2)," where amino acid residues in square brackets indicate acceptable amino acids, numbers in parentheses indicate the number of amino acid residues, "X$_1$" represents Phe-(p-CH$_2$)SO$_3$H, "X$_2$" represents sulfated tyrosine, and "X$_3$" represents 2-sulfotyrosine (SEQ ID NO:126). Additional examples of complement C1s inhibitors include a peptide or polypeptide that inhibits complement C1s, wherein the peptide or polypeptide comprises the amino acid sequence "CRLGC" (amino acid residues 64 to 68 of SEQ ID NO:1), and wherein the peptide or polypeptide consists of five to thirty amino acid residues. For example, a suitable polypeptide consists of the amino acid sequence: "GCDGFKCRLG CTYGFKTDKK GCEAFCTCNT" (SEQ ID NO:53), whereas a suitable peptide consists of the amino acid sequence: "CRLGC."

The present invention further includes complement C1s inhibitors, wherein the inhibitors consist of:
(a) a C1s catalytic site-directed moiety (CCSDM), which is selected from the group consisting of: (i) CH$_3$-Lys (Cbo)-Gly-Arg-pNA-AcOH, where "Cbo" represents benzyloxycarbonyl; (ii) CH$_3$-Lys(Cbo)-Gly-Arg; (iii) H-D-Val-Ser-Arg-pNA·HCl; (iv) H-D-Val-Ser-Arg; (v) Leu-Xaa-Arg, where "Xaa" represents alanine, glutamine, or glycine;

(vi) LQRALEILPN RVTIKANRPF LVFI    (SEQ ID NO:118), (vii) serine protease inhibitor; (viii) heterocyclic protease inhibitor; (ix) transition state analogue; (x) benzamidine; (xi) X-C1-C2-A-Y, where C1 is a derivative of Arg, Lys, or Orn, characterized by a reduced carboxylate moiety or a carboxylate moiety that is displaced from the α-carbon by a chemical structure characterized by a backbone chain of from 1 to 10 atoms, C2 is a non-cleavable bond, "X" is hydrogen or a continuation of the peptide backbone, "A" is a backbone chain, and "Y" is a bond; (xii)

(SEQ ID NO:121);
(xii) CDGFK CRLGC TYGFK TDKKG CEAFC TCNT and (xiii) X-C-X(8-12)-L-Q-R, where "X" represents glycine, serine, or threonine, and numbers in parentheses indicate the number of amino acid residues (SEQ ID NO:140);
(b) a linker moiety that is either characterized by a backbone chain having a calculated length of between 14 Å and 20 Å, or that is a polypeptide, which has the amino acid sequence of (SEQ ID NO:123);
KETAC VNIWC TDPYK CNPES GRCED and
(c) a C1s exosite binding moiety (CEBM), which is selected from the group consisting of: (i) a polypeptide characterized by the formula: "[AP]-N-[DE](2)-[YX$_1$X$_2$X$_3$]-[DE](1,2)-[YX$_1$X$_2$X$_3$]-[DE]-[YX$_1$X$_2$X$_3$]-[DE](1,2)," where amino acid residues in square brackets indicate acceptable amino acids, numbers in parentheses indicate the number of amino acid residues, "X$_1$" represents Phe-(p-CH2)SO$_3$H, "X$_2$" represents sulfated tyrosine, and "X$_3$" represents 2-sulfotyrosine (SEQ ID NO:126); and (ii) NEDYEDYEYD (SEQ ID NO:119);

wherein the C1s catalytic site-directed moiety is bound to the linker moiety, the linker moiety is bound to the C1s exosite binding moiety.

Suitable CCSDM moieties include serine protease inhibitors selected from the group consisting of phenylmethylsulfonylfluoride, diisopropylflouorophosphate, tosylprolylchloromethylketone, and tosyllysl chloromethylketone. An illustrative heterocyclic protease inhibitor is an isocoumarin, and an exemplary transition state analogue is difluoroketomethylene. Inhibitors comprising a CCSDM moiety with the formula "X-C1-C2-A-Y" include a C1 component selected from the group consisting of β-homoarginine, an arginine containing a reduced carboxylate moiety, and β-homoornithine. An illustrative arginine that contains a reduced carboxylate moiety is Argψ[CH₂NH]. Illustrative linkers include linkers selected from the group consisting of:

```
(i)    A-L-[ED]-[ED]-X(1-3)    (SEQ ID NO:131),
(ii)   A-L-X(1-3)-[ED]-[ED]    (SEQ ID NO:132),
(iii)  A-L-[ED]-[ED]           (SEQ ID NO:122),
(iv)   X(2-5)-[ED]-[ED]        (SEQ ID NO:134),
(v)    A-L-[ED]-[ED]-X(1-2)-C  (SEQ ID NO:136),
(vi)   A-L-[ED]-[ED]-C         (SEQ ID NO:124),
(vii)  X(1-4)-[ED]-[ED]-C      (SEQ ID NO:138),
(viii) A-L-X(1-2)-[ED]-[ED]-C  (SEQ ID NO:139),
(ix)   X(4-7)                  (SEQ ID NO:133),
(x)    X(5-7)                  (SEQ ID NO:135), and
(xi)   X(3-6)-C                (SEQ ID NO:137),
``` where amino acid residues in square brackets indicate acceptable amino acids, numbers in parentheses indicate the number of amino acid residues, and "X" represents any of glycine, serine, or threonine.

The present invention also contemplates complement C1s inhibitors, wherein the inhibitors consist of:

(a) a C1s catalytic site-directed moiety (CCSDM), which is selected from the group consisting of:

```
(i) GCDGFKCRLG CTYGFKTDKK GCEAECTCNT (SEQ ID NO:53)
``` and

```
(ii) CRLGC (amino acid residues 64 to 68 of
SEQ ID NO:1);
```

(b) a linker moiety characterized by a backbone chain having a calculated length of between 14 Å and 20 Å; and (c) a C1s exosite binding moiety (CEBM), which is a polypeptide characterized by the formula: "A-N-[DE](2)-[YX₁X₂X₃]-[DE](1,2)-[YX₁X₂X₃]-[DE]-[YX₁X₂X₃]-[DE](1,2)," where amino acid residues in square brackets indicate acceptable amino acids, numbers in parentheses indicate the number of amino acid residues, "X₁" represents Phe-(p-CH2)SO₃H, "X₂" represents sulfated tyrosine, "X₃" represents 2-sulfotyrosine (SEQ ID NO:128);

wherein the C1s catalytic site-directed moiety is bound to the linker moiety, the linker moiety is bound to the C1s exosite binding moiety.

Inhibitors comprising multiple functional moieties, as described above, can be characterized by the formula: "CCSDM-Linker-CEBM."

The present invention also provides compositions that comprise a carrier, and a peptide, or a polypeptide, described herein, as well as methods for inhibiting complement C1s inhibitor, comprising the administration of such compositions. These compositions can be administered to a mammalian subject, such as a farm animal, a domestic animal, or a human patient.

These and other aspects of the invention will become evident upon reference to the following detailed description. In addition, various references are identified below and are incorporated by reference in their entirety.

2. DEFINITIONS

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence.

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

A "cloning vector" is a nucleic acid molecule, such as a plasmid, cosmid, or bacteriophage, which has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces a complement C1s inhibitory peptide or polypeptide from an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a complement C1s inhibitor fused with a polypeptide that binds an affinity matrix. Such a fusion protein provides a means to isolate large quantities of a complement C1s inhibitor using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

The term "secretory signal sequence" denotes a nucleotide sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. If subsequent dissociation of the complement/anti-complement pair is desirable, then the complement/anti-complement pair preferably is characterized by a binding affinity of less than $10^9$ $M^{-1}$.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). Nucleic acid molecules encoding affinity tags are available from commercial suppliers (e.g., Pharmacia Biotech, Piscataway, N.J.).

Due to the imprecision of standard analytical methods, molecular weights and lengths of polymers are understood to be approximate values. When such a value is expressed as "about" X or "approximately" X, the stated value of X will be understood to be accurate to ±10%.

3. Synthetic Complement C1s Inhibitory Peptides and Polypeptides

A. C1s Exosite Binding Moiety

One series of peptides, designed to bind the exosite region of C1s, are derived from the C-terminus of BD001, or the C-terminus of C4. These peptides may include tyrosine residues that lack sulfation, or one or more tyrosine residues that are sulfated. If tyrosine sulfation is desired, then peptides can contain either sulfated tyrosine or an analog of sulfated tyrosine. An example of a tyrosine sulfate analog is Phe-(p-CH$_2$)SO$_3$H. Methods for synthesizing this analog are known to those of skill in the art (see, for example, Gonzalez-Muniz et al., *Int. J. Peptide Protein Res.* 37:331 (1991)).

The following formula describes one suitable class of C1s exosite binding moieties: "[AP]-N-[DE](2)-[YX$_1$X$_2$X$_3$]-[DE](1,2)-[YX$_1$X$_2$X$_3$]-[DE]-[YX$_1$X$_2$X$_3$]-[DE](1,2)," where amino acid residues in square brackets indicate acceptable amino acids, numbers in parentheses indicate the number of amino acid residues, "X$_1$," represents sulfated phenylalanine (Phe-(p-CH$_2$)SO$_3$H), "X$_2$" represents sulfated tyrosine (Tyr (OSO$_3$H)), and "X$_3$" represents 2-sulfotyrosine (SEQ ID NO:126) Examples of C1s exosite binding polypeptides are provided in Table 1 and Table 2. Such polypeptides can include tyrosine residues that are non-sulfated or sulfated. Those of skill in the art using the above formula can devise additional polypeptides. The activity of these polypeptides can be assessed by measuring the ability to inhibit a classical complement hemolysis assay, such as the assay presented in Example 1.

The compounds referred to as sulfated phenylalanine, sulfated tyrosine, and 2-sulfotyrosine have the structural formulae:

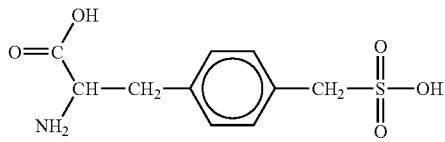

Sulfated phenylalanine

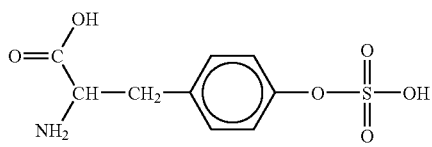

Sulfated tyrosine

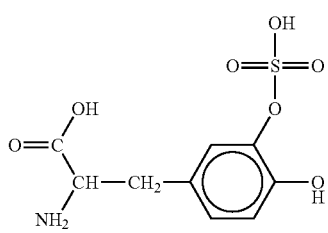

2-Sulfotyrosine

TABLE 1

| Amino Acid Sequence[1] | SEQ ID NO |
|---|---|
| P-N-E-E-Y-E-Y-D-Y-E | 2 |
| P-N-E-E-$X_1$-E-Y-D-Y-E | 3 |
| P-N-E-E-Y-E-$X_1$-D-Y-E | 4 |
| P-N-E-E-Y-E-Y-D-$X_1$-E | 5 |
| P-N-E-E-$X_1$-E-$X_1$-D-Y-E | 6 |
| P-N-E-E-$X_1$-E-Y-D-$X_1$-E | 7 |
| P-N-E-E-Y-E-$X_1$-D-$X_1$-E | 8 |
| P-N-E-E-$X_1$-E-$X_1$-D-$X_1$-E | 9 |
| P-N-E-E-$X_2$-E-Y-D-Y-E | 10 |
| P-N-E-E-Y-E-$X_2$-D-Y-E | 11 |
| P-N-E-E-Y-E-Y-D-$X_2$-E | 12 |
| P-N-E-E-$X_2$-E-$X_2$-D-Y-E | 13 |
| P-N-E-E-$X_2$-E-Y-D-$X_2$-E | 14 |
| P-N-E-E-Y-E-$X_2$-D-$X_2$-E | 15 |
| P-N-E-E-$X_2$-E-$X_2$-D-$X_2$-E | 16 |
| P-N-E-E-$X_1$-E-$X_2$-D-Y-E | 17 |
| P-N-E-E-$X_2$-E-$X_1$-D-Y-E | 18 |
| P-N-E-E-$X_1$-E-Y-D-$X_2$-E | 19 |
| P-N-E-E-$X_2$-E-Y-D-$X_1$-E | 20 |
| P-N-E-E-Y-E-$X_1$-D-$X_2$-E | 21 |
| P-N-E-E-Y-E-$X_2$-D-$X_1$-E | 22 |
| P-N-E-E-$X_1$-E-$X_1$-D-$X_2$-E | 23 |
| P-N-E-E-$X_2$-E-$X_1$-D-$X_1$-E | 24 |
| P-N-E-E-$X_1$-E-$X_2$-D-$X_2$-E | 25 |
| P-N-E-E-$X_1$-E-$X_2$-D-$X_1$-E | 26 |
| P-N-E-E-$X_2$-E-$X_2$-D-$X_1$-E | 27 |

[1]Abbreviations:
$X_1$ = Phe-(p-$CH_2$)$SO_3$H,
$X_2$ = sulfated tyrosine.

TABLE 2

| Amino Acid Sequence[1] | SEQ ID NO |
|---|---|
| A-N-E-D-$X_1$-E-D-Y-E-Y-D | 28 |
| A-N-E-D-Y-E-D-$X_1$-E-Y-D | 29 |
| A-N-E-D-Y-E-D-Y-E-$X_1$-D | 30 |
| A-N-E-D-X-E-D-$X_1$-E-Y-D | 31 |
| A-N-E-D-$X_1$-E-D-Y-E-$X_1$-D | 32 |
| A-N-E-D-Y-E-D-$X_1$-E-$X_1$-D | 33 |
| A-N-E-D-$X_1$-E-D-$X_1$-E-$X_1$-D | 34 |
| A-N-E-D-$X_2$-E-D-Y-E-Y-D | 35 |
| A-N-E-D-Y-E-D-$X_2$-E-Y-D | 36 |
| A-N-E-D-Y-E-D-Y-E-$X_2$-D | 37 |
| A-N-E-D-$X_2$-E-D-$X_2$-E-Y-D | 38 |
| A-N-E-D-$X_2$-E-D-Y-E-$X_2$-D | 39 |
| A-N-E-D-Y-E-D-$X_2$-E-$X_2$-D | 40 |
| A-N-E-D-$X_2$-E-D-$X_2$-E-$X_2$-D | 41 |
| A-N-E-D-$X_1$-E-D-$X_2$-E-Y-D | 42 |
| A-N-E-D-$X_2$-E-D-$X_1$-E-Y-D | 43 |
| A-N-E-D-$X_1$-E-D-Y-E-$X_2$-D | 44 |
| A-N-E-D-$X_2$-E-D-Y-E-$X_1$-D | 45 |
| A-N-E-D-Y-E-D-$X_1$-E-$X_2$-D | 46 |
| A-N-E-D-Y-E-D-$X_2$-E-$X_1$-D | 47 |
| A-N-E-D-$X_1$-E-D-$X_1$-E-$X_2$-D | 48 |
| A-N-E-D-$X_2$-E-D-$X_1$-E-$X_1$-D | 49 |
| A-N-E-D-$X_1$-E-D-$X_2$-E-$X_2$-D | 50 |
| A-N-E-D-$X_1$-E-D-$X_2$-E-$X_1$-D | 51 |
| A-N-E-D-$X_2$-E-D-$X_2$-E-$X_1$-D | 52 |

[1]Abbreviations:
$X_1$ = Phe-(p-$CH_2$)$SO_3$H,
$X_2$ = sulfated tyrosine.

B. C1s Catalytic Site-Directed Moiety

Studies were performed to localize the active site of BD001. In one group of experiments, BD001 was incubated with C1s to cleave BD001, and then cleaved BD001 was fractionated using SDS-polyacrylamide gel electrophoresis. Fractionated protein fragments were then electro-blotted onto nitrocellulose, and sequenced using standard Edman degradation. The results revealed the presence of fragments consisting of an amino acid sequence that included the N-terminus of BD001 to amino acid residue 66. Accordingly, one type of C1s catalytic site-directed moiety is a peptide or polypeptide comprising amino acid residues 64 to 68 of SEQ ID NO:1. An illustrative polypeptide comprises the following amino acid sequence:

GCDGFKCRLG CTYGFKTDKK GCEAFCTCNT (SEQ ID NO:53).

Additional amino acid sequences are presented in Table 3. Certain of these C1s catalytic site-directed moieties are variations of SEQ ID NO:53 in which cysteine residues have been replaced by serine residues. In particular embodiments, these serine-substituted polypeptides are oxidized to induce the formation of disulfide bonds.

TABLE 3

| Amino Acid Sequence | SEQ ID NO |
|---|---|
| GCDGFKCRLGCTYGFKTDKKGCEAFCTCNT | 53 |
| GCDGFKSRLGSTYGFKTDKKGCEAFSTSNT | 54 |
| GSDGFKCRLGSTYGFKTDKKGSEAFCTSNT | 55 |
| GSDGFKSRLGCTYGFKTDKKGSEAFSTCNT | 56 |
| GCDGFKSRLGCTYGFKTDKKGCEAFCTCNT | 57 |
| GCDGFKCRLGSTYGFKTDKKGCEAFCTCNT | 58 |
| GCDGFKCRLGCTYGFKTDKKGCEAFSTCNT | 59 |
| GCDGFKCRLGCTYGFKTDKKGCEAFCTSNT | 60 |
| GCDGFKSRLGSTYGFKTDKKGCEAFCTCNT | 61 |
| GCDGFKSRLGCTYGFKTDKKGCEAFSTCNT | 62 |
| GCDGFKSRLGCTYGFKTDKKGCEAECTSNT | 63 |
| GCDGFKCRLGSTYGFKTDKKGCEAFSTCNT | 64 |
| GCDGFKCRLGSTYGFKTDKKGCEAECTSNT | 65 |
| GCDGFKCRLGCTYGFKTDKKGCEAFSTSNT | 66 |
| GCDGFKSRLGCTYGFKTDKKGCEAFSTCNT | 67 |
| GCDGFKSRLGSTYGFKTDKKGCEAFCTSNT | 68 |
| GCDGFKCRLGCTYGFKTDKKGCEAFSTSNT | 69 |
| GCDGFKSRLGSTYGFKTDKKGCEAFSTSNT | 70 |
| GSDGFKCRLGCTYGFKTDKKGCEAFCTCNT | 71 |
| GCDGFKCRLGSTYGFKTDKKGCEAFCTCNT | 72 |
| GCDGFKCRLGCTYGFKTDKKGSEAFCTCNT | 73 |
| GCDGFKCRLGCTYGFKTDKKGCEAFCTSNT | 74 |
| GSDGFKCRLGSTYGFKTDKKGCEAECTCNT | 75 |
| GSDGFKCRLGCTYGFKTDKKGSEAFCTCNT | 76 |
| GSDGFKCRLGCTYGFKTDKKGCEAFCTSNT | 77 |
| GCDGFKCRLGSTYGFKTDKKGSEAFCTCNT | 78 |
| GCDGFKCRLGSTYGFKTDKKGCEAFCTSNT | 79 |
| GCDGFKCRLGCTYGFKTDKKGSEAFCTSNT | 80 |
| GSDGFKCRLGSTYGFKTDKKGSEAECTCNT | 81 |
| GSDGFKCRLGCTYGFKTDKKGSEAFCTSNT | 82 |
| GCDGFKCRLGSTYGFKTDKKGSEAFCTSNT | 83 |
| GCDGFKCRLGSTYGFKTDKKGCEAECTSNT | 84 |
| GSDGFKCRLGCTYGFKTDKKGCEAFCTCNT | 85 |
| GCDGFKSRLGCTYGFKTDKKGCEAFCTCNT | 86 |
| GCDGFKCRLGCTYGFKTDKKGSEAECTCNT | 87 |
| GCDGFKCRLGCTYGFKTDKKGCEAFSTCNT | 88 |
| GSDGFKSRLGCTYGFKTDKKGCEAECTCNT | 89 |
| GSDGFKCRLGCTYGFKTDKKGSEAFCTCNT | 90 |
| GSDGFKCRLGCTYGFKTDKKGCEAFSTCNT | 91 |
| GCDGFKSRLGCTYGFKTDKKGSEAFCTCNT | 92 |
| GCDGFKSRLGCTYGFKTDKKGCEAESTCNT | 93 |
| GCDGFKCRLGCTYGFKTDKKGSEAFSTCNT | 94 |
| GSDGFKSRLGCTYGFKTDKKGSEAECTCNT | 95 |
| GSDGFKSRLGCTYGFKTDKIKGCEAESTCNT | 96 |
| GCDGFKSRLGCTYGFKTDKKGSEAFSTCNT | 97 |
| GSDGFKCRLGCTYGFKTDKKGSEAFSTCNT | 98 |

A C1s catalytic site-directed moiety can also consist of the amino acid sequence CRLGC (amino acid residues 64 to 68 of SEQ ID NO:1). In addition, a C1s catalytic site-directed moiety can comprise a peptide or polypeptide shown in Table 4. Those of skill in the art can devise further modifications of the sequences disclosed herein.

TABLE 4

| Amino Acid Sequence | SEQ ID NO |
|---|---|
| CRLGCT | 99 |
| CRLGCTY | 100 |
| CRLGCTYG | 101 |
| CRLGCTYGF | 102 |
| CRLGCTYGFK | 103 |
| CRLGCTYGFKT | 104 |
| CRLGCTYGFKTD | 105 |
| CRLGCTYGFKTDK | 106 |
| CRLGCTYGFKTDKK | 107 |

TABLE 4-continued

| Amino Acid Sequence | SEQ ID NO |
|---|---|
| CRLGCTYGFKTDKKG | 108 |
| CRLGCTYGFKTDKKGC | 109 |
| CRLGCTYGFKTDKKGCE | 110 |
| CRLGCTYGFKTDKKGCEA | 111 |
| CRLGCTYGFKTDKKGCEAF | 112 |
| CRLGCTYGFKTDKKGCEAFC | 113 |
| CRLGCTYGFKTDKKGCEAECT | 114 |
| CRLGCTYGFKTDKKGCEAECTC | 115 |
| CRLGCTYGFKTDKKGCEAECTCN | 116 |

C. Bivalent Polypeptide Inhibitors

Bivalent polypeptide inhibitors comprise a C1s catalytic site-directed moiety, a linker, and a C1s exosite binding moiety. Various C1s catalytic site-directed moieties, described above, can be used for bivalent inhibitors. Additional useful catalytic site-directed moieties include molecules that are cleaved by C1s. For example, Pefachrome C1E (Pentapharm; Basel, Switzerland) is a para-nitroaniline (pNA) containing substrate, which is cleaved by C1s to release free pNA. Pefachrome C1E has the following sequence, in which "Cbo" represents benzyloxycarbonyl: $CH_3$-Lys(Cbo)-Gly-Arg-pNA·AcOH. A derivative of Pefachrome C1E that would be suitable as a catalytic site-directed moiety is: $CH_3$-Lys(Cbo)-Gly-Arg. As another example, S-2314 (Chromogenix; Milano, Italy) is a colorimetric substrate, which is cleaved by C1s, and which has the following sequence: H-D-Val-Ser-Arg-pNA·HCl. A derivative of this molecule, which would be suitable as a catalytic site-directed moiety is: H-D-Val-Ser-Arg.

Those of skill in the art can devise additional catalytic site-directed moieties from known C1s substrates. As an illustration, the following sequence appears to be a recognition site in human C4 that confers specificity for C1s:

LQRALE        (SEQ ID NO:117).

The cleavage site is located between the Arg and Ala, and the downstream residues appear to be important for recognition by C1s (see, for example, Ogata et al., *Proc. Nat'l Acad. Sci. USA.* 86:5575 (1989), and Ogata and Low, *J. of Immunol.* 155:2642 (1995)). Based upon studies with closely related complement proteins C3, C4, C5, and sex-limited protein, researchers have suggested that the minimally required active site sequence is: Leu-Xaa-Arg, where Xaa is Ala, Gln, or Gly. Accordingly, such sequences can provide suitable C1s catalytic-site directed moieties.

Researchers have shown that the cleavage site of C4 can inhibit the classical complement pathway when linked to the C-terminal portion of antithrombin III (Glover et al., *Molec. Immunol.* 25:1261 (1988); Schasteen et al., *Molec. Immunol.* 25:1269 (1988)). The polypeptide, which has the sequence

LQRALEILPN RVTIKANRPF LVFI  (SEQ ID NO:118), is another suitable C1s catalytic site-directed moiety.

Catalytic site-directed moieties can be designed to bind irreversibly to C1s protease. Examples of such irreversible active site inhibitors include general serine protease inhibitors (e.g., phenylmethylsulfonylfluoride, diisopropylflouorophosphate, tosylprolylchloromethylketone, tosyllysl chloromethylketone, etc.), heterocyclic protease inhibitors, such as isocoumarins, and transition state analogues, such as difluoroketomethylene.

Another type of catalytic site-directed moiety can consist of non-cleavable, reversible active site inhibitors. One example of a useful non-cleavable reversible active site inhibitor is benzamidine. As another example, inhibitors can be characterized by the formula: X-C1-C2-A-Y, where C1 is a derivative of Arg, Lys, or Orn, characterized by a reduced carboxylate moiety or a carboxylate moiety that is displaced from the α-carbon by a chemical structure characterized by a backbone chain of from 1–10 atoms; C2 is a non-cleavable bond; X is hydrogen or a continuation of the peptide backbone; A is a backbone chain; and Y is a bond. Examples of C1 components include β-homoarginine; arginine containing a reduced carboxylate moiety, such as Argψ[$CH_2NH$]; β-homolysine; and β-homoornithine. Methods for synthesizing such analogues are known to those of skill in the art. For example, Steinmetzer et al., *J. Med. Chem.* 42:3109 (1999), describe methods for incorporating various arginyl ketomethylene isosteres (Argψ[$CO-CH_2$-X]$P_1$') into polypeptides as $P_1$–$P_1$' segments to eliminate the scissile bond, where $P_1$' can be a natural or an unnatural amino acid.

Illustrative C1s exosite binding moieties include the molecules described above, as well as the polypeptide

NEDYEDYEYD       (SEQ ID NO:119).

Computer modeling studies revealed that suitable linkers of bivalent polypeptide inhibitors have a backbone chain with a calculated length of about 14 Å to about 20 Å, about 15 Å to about 19 Å, or about 16 Å to about 18 Å (e.g., 14 Å to 20 Å, 15 Å to 19 Å, or 16 Å to 18 Å). The term "backbone chain" refers to the portion of a chemical structure that defines the smallest number of consecutive bonds that can be traced from one end of the structure to the other end. A backbone chain can comprise atoms capable of forming bonds with at least two other atoms. The term "calculated length" refers to a measurement derived by summing up the bond lengths between the atoms, which comprise the backbone chain. Linkers are also contemplated that include certain protein domains, such as a linker comprising the amino acid sequence

"KETACVNIWC TDPYKCNPES GRC"  (SEQ ID NO:120).

Suitable linkers include peptides comprised of about two to about nine amino acids, about four to about seven amino acids, about five to seven amino acids, or six to seven amino acids. Illustrative combinations of C1s catalytic site-directed moieties and linkers are provided in Table 5.

TABLE 5

| C1s catalytic site-directed moiety[1] | Linker[1] |
|---|---|
| L-Q-R | A-L-[ED]-[ED]-X(1-3)<br>(SEQ ID NO:131) |
| Benzamidine | A-L-X(1-3)-[ED]-[ED]<br>(SEQ ID NO:132)<br>A-L-[ED]-[ED](SEQ ID NO:122)<br>X(4-7) (SEQ ID NO:133)<br>X(2-5)-[ED]-[ED](SEQ ID NO:134) |
| C-D-G-F-K-C-R-L-G-C-T-Y-G-F-K-<br>T-D-K-K-G-C-E-A-F-C-T-C-N-T<br>(SEQ ID NO:121) | K-E-T-A-C-V-N-I-W-C-T-D-P-Y<br>K-C-N-P-E-S-G-R-C-E-D<br>(SEQ ID NO:123)<br>X(5-7) (SEQ ID NO:135)<br>A-L-[ED]-[ED]-X(1-3)<br>(SEQ ID NO:131)<br>A-L-X(1-3)-[ED]-[ED]<br>(SEQ ID NO:132) |
| X-C-X(8-12)-L-Q-R<br>(SEQ ID NO:140) | A-L-[ED]-[ED]-X(1-2)-C<br>(SEQ ID NO:136)<br>A-L-[ED]-[ED]-C<br>(SEQ ID NO:124)<br>X(3-6)-C (SEQ ID NO:137)<br>X(1-4)-[ED]-[ED]-C<br>(SEQ ID NO:138)<br>A-L-X(1-2)-[ED]-[ED]-C<br>(SEQ ID NO:139) |

[1]Amino acid residues in square brackets indicate acceptable amino acids; "X" represents any of glycine, serine, or threonine; numbers in parentheses indicate the number of amino acid residues.

Bivalent polypeptide inhibitors can be produced synthetically or recombinantly, as described below. Alternatively, bivalent polypeptide inhibitors can be assembled by conjugating synthetically- or recombinantly-produced C1s catalytic site-directed and C1s exosite binding moieties with linkers. Well-known methods of conjugating polypeptides are described by Lappi et al., *Biochem. Biophys. Res. Commun.* 160:917 (1989), Wong, *Chemistry of Protein Conjugation and Cross-Linking* (CRC Press 1991), Soria et al., *Targeted Diagn. Ther.* 7:193 (1992), Buechler et al., *Eur. J. Biochem.* 234:706 (1995), Behar-Cohen et al., *Invest. Ophthalmol. Vis. Sci.* 36:2434 (1995), Lappi and Baird, U.S. Pat. No. 5,191,067, Calabresi et al., U.S. Pat. No. 5,478,804, and Lappi and Baird, U.S. Pat. No. 5,576,288. Additional approaches to conjugating polypeptides are known to those of skill in the art.

In certain embodiments, either the carboxy-terminus or the amino-terminus, or both, are chemically modified. For example, terminal amino groups can be acetylated, whereas carboxyl groups can be amidated. Amino-terminal modifications such as acylation (e.g., acetylation) or alkylation (e.g., methylation) and carboxy-terminal modifications such as amidation, as well as other terminal modifications, including cyclization, may be incorporated into peptides and polypeptides described herein.

The present invention also includes complement inhibitors that do not comprise only naturally occurring amino acids. In general, such "peptidomimetics" are structurally similar to a model inhibitory peptide or polypeptide, but have one or more peptide linkages optionally replaced by a linkage such as: —$CH_2NH$—, —$CH_2S$—, —$CH_2$—$CH_2$—, —CHCH— (cis and trans), —$COCH_2$—, —CH(OH)$CH_2$—, —$CH_2SO$—, and the like. Methods for preparing such polypeptide analogs are known to those of skill in the art (see, for example, Kazmierski (Ed.), *Peptidomimetics Protocols* (Humana Press, Inc. 1998); Abel (Ed.), *Advances in Amino Acid Mimetics and Peptidomimetics* (JAI Press, 1999)).

Examples of suitable non-naturally occurring amino acids include norleucine, alloisoleucine, homoarginine, thiaproline, dehydroproline, homoserine, cyclohexylglycine-amino-n-butyric acid, cyclohexylalanine, aminophenylbutyric acid, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, 4-fluorophenylalanine, phenylalanines substituted at the ortho, meta, or para position of the phenyl moiety with one or two of the following: a ($C_1$–$C_4$) alkyl, a ($C_1$–$C_4$) alkoxy, halogen, or nitro groups or substituted with a methylenedioxy group; β-2- and 3-thienylalanine, β-2- and 3-furanylalanine, β-2-, 3- and 4-pyridylalanine, β-(benzothienyl- 2- and 3yl)alanine, β-(1- and 2-naphthyl)alanine, O-alkylated derivatives of serine, threonine, or tyrosine, S-alkylated cysteine, S-alkylated homocysteine, O-sulfate, O-phosphate, and O-carboxylate esters of tyrosine, 3- and 5-sulfonyl tyrosine, 3- and 5-carbonyl tyrosine, 3- and 5-phosphonyl tyrosine, 4-methylsulfonyl tyrosine, 4-methylphosphonyl tyrosine, 4-phenylacetic acid, 3,5-diiodotyrosine, 3- and 5-nitrotyrosine, ε-alkyl lysine, delta-alkyl ornithine, and the like, as well as D-isomers of the naturally occurring amino acids.

Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

Those of skill in the art devise additional variations of C1s exosite binding moieties, linkers, and C1s catalytic site-directed moieties described herein. For example, a systematic substitution of one or more amino acids with a D-amino acid of the same type (e.g., D-lysine in place of L-lysine) can be used to generate more stable peptides. In addition, constrained peptides (including cyclized peptides) can be generated by methods known in the art (see, for example, Rizo and Gierasch, *Ann. Rev. Biochem.* 61: 387 (1992)).

The biological activity of C1s exosite binding moieties, C1s catalytic site-directed moieties, and bivalent inhibitor polypeptides can be tested in a variety of assays. Example 1 illustrates several approaches. In addition, a simple standard assay for C1-esterase inhibitor activity can be based upon the ability of a test substance to block the production of a chromogenic proteolytic product following the addition of purified C1s to plasma, as described by Wiman and Nilsson, *Clin. Chem. Acta* 128:359 (1983). Another standard approach requires the kinetic measurement of a putative C1s inhibitor as it inhibits the hydrolysis of N-acetyl-L-tyrosine-ethyl ester by C1 esterase (Schena et al., *J. Clin. Chem. Clin. Biochem.* 18:17 (1980)). Additional assays can be devised by those of skill in the art.

4. Chemical Synthesis and Semi-synthesis of Complement C1s Inhibitory Peptides and Polypeptides Inhibitory peptides and polypeptides of the present invention can be synthesized using standard techniques, including solid phase synthesis, partial solid phase methods, fragment condensation, or classical solution synthesis. The polypeptides can be prepared by solid phase peptide synthesis, for example as described by Merrifield, *J. Am. Chem. Soc.* 85:2149 (1963). The synthesis is carried out with amino acids that are protected at the α-amino terminus. Trifunctional amino acids with labile side-chains are also protected with suitable groups to prevent undesired chemical reactions from occurring during the assembly of the polypeptides. The α-amino protecting group is selectively removed to allow subsequent reaction to take place at the amino-terminus. The conditions for the removal of the α-amino protecting group do not remove the side-chain protecting groups.

The α-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxy-carbonyl (Fmoc)], aliphatic urethane protecting groups [e.g., t-butyloxycarbonyl (tBoc), isopropyloxycarbonyl, cyclohexloxycarbonyl] and alkyl type protecting groups (e.g., benzyl, triphenylmethyl). The preferred protecting groups are tBoc and Fmoc, thus the peptides are said to be synthesized by tboc and Fmoc chemistry, respectively.

The side-chain protecting groups selected must remain intact during coupling and not be removed during the deprotection of the amino-terminus protecting group or during coupling conditions. The side-chain protecting groups must also be removable upon the completion of synthesis using reaction conditions that will not alter the finished polypeptide. In tBoc chemistry, the side-chain protecting groups for trifunctional amino acids are mostly benzyl based. In Fmoc chemistry, they are mostly tert-butyl or trityl based.

In tBoc chemistry, the preferred side-chain protecting groups are tosyl for arginine, cyclohexyl for aspartic acid, 4-methylbenzyl (and acetamidomethyl) for cysteine, benzyl for glutamic acid, serine and threonine, benzyloxymethyl (and dinitrophenyl) for histidine, 2-Cl-benzyloxycarbonyl for lysine, formyl for tryptophan and 2-bromobenzyl for tyrosine. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf) for arginine, trityl for asparagine, cysteine, glutamine and histidine, tert-butyl for aspartic acid, glutamic acid, serine, threonine and tyrosine, tboc for lysine and tryptophan.

For the synthesis of phosphopeptides, either direct or post-assembly incorporation of the phosphate group is used. In the direct incorporation strategy, the phosphate group on serine, threonine or tyrosine may be protected by methyl, benzyl, or tert-butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl groups of serine, threonine or tyrosine are derivatized on solid phase with di-tert-butyl-, dibenzyl- or dimethyl-N,N'-diisopropylphosphoramidite and then oxidized by tert-butylhydroperoxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortrityl or hydroxymethyl resin, and the resulting polypeptide will have a free carboxyl group at the C-terminus. Alternatively, when an amide resin such as benzhydrylamine or p-methylbenzhydrylamine resin (for tBoc chemistry) and Rink amide or PAL resin (for Fmoc chemistry) are used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), and by Lloyd-Williams et al., *Chemical Approaches to the Synthesis of Peptides and Proteins* (CRC Press, Inc. 1997).

The C-terminal amino acid, protected at the side chain if necessary, and at the alpha-amino group, is attached to a hydroxylmethyl resin using various activating agents including dicyclohexylcarbodiimide (DCC), N,N'-diisopropylcarbodiimide (DIPCDI) and carbonyldiimidazole (CDI). It can be attached to chloromethyl or chlorotrityl resin directly in its cesium tetramethylammonium salt form or in the presence of triethylamine (TEA) or diisopropylethylamine (DIEA). First amino acid attachment to an amide resin is the same as amide bond formation during coupling reactions.

Following the attachment to the resin support, the α-amino protecting group is removed using various reagents depending on the protecting chemistry (e.g., tBoc, Fmoc). The extent of Fmoc removal can be monitored at 300–320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxytris-(dimethylamino)-phosphonium hexafluoro-phosphate (BOP) and its pyrrolidine analog (PyBOP), bromo-tris-pyrrolidino-phosphonium hexafluorophosphate (PyBroP), O-(benzotriazol-1-yl)-1,1,3,3-tetramethyl-uronium hexafluorophosphate (HBTU) and its tetrafluoroborate analog (TBTU) or its pyrrolidine analog (HBPyU), O-(7-azabenzotriazol-1-yl)-1,1,3,3-tetramethyl-uronium hexafluorophosphate (HATU) and its tetrafluoroborate analog (TATU) or its pyrrolidine analog (HAPyU). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidone (NMP) or in DMF, CH2Cl2 or mixtures thereof. The extent of completion of the coupling reaction can be monitored at each stage, e.g., by the ninhydrin reaction as described by Kaiser et al., *Anal. Biochem.* 34:595 (1970). In cases where incomplete coupling is found, the coupling reaction is extended and repeated and may have chaotropic salts added. The coupling reactions can be performed automatically with commercially available instruments such as ABI model 430A, 431A and 433A peptide synthesizers.

After the entire assembly of the desired peptide, the peptide-resin is cleaved with a reagent with proper scavengers. The Fmoc peptides are usually cleaved and deprotected by TFA with scavengers (e.g., water, ethanedithiol, phenol and thioanisole). The tBoc peptides are usually cleaved and deprotected with liquid HF for 1–2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of tryptophan and the dinitrophenyl group of histidine need to be removed, respectively by piperidine and thiophenyl in DMF prior to the HF cleavage. The acetamidomethyl group of cysteine can be removed by mercury(II)acetate and alternatively by iodine, thallium(III)trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

The "native chemical ligation" approach to producing polypeptides is one variation of total chemical synthesis strategy (see, for example, Dawson et al., *Science* 266:776 (1994), Hackeng et al., *Proc. Nat'l Acad. Sci. USA* 94:7845 (1997), and Dawson, *Methods Enzymol.* 287:34 (1997)). According to this method, an N-terminal cysteine-containing peptide is chemically ligated to a peptide having a C-terminal thioester group to form a normal peptide bond at the ligation site.

The "expressed protein ligation" method is a semi-synthesis variation of the ligation approach (see, for example, Muir et al, *Proc. Nat'l Acad. Sci. USA* 95:6705 (1998); Severinov and Muir, *J. Biol. Chem.* 273:16205 (1998)). Here, synthetic peptides and protein cleavage fragments are linked to form the desired protein product. This method is particularly useful for the site-specific incorporation of unnatural amino acids (e.g., amino acids comprising biophysical or biochemical probes) into proteins.

In an approach illustrated by Muir et al, *Proc. Nat'l Acad. Sci. USA* 95:6705 (1998), a gene or gene fragment is cloned into the PCYB2-IMPACT vector (New England Biolabs, Inc.; Beverly, Mass.) using the NdeI and SmaI restriction sites. As a result, the gene or gene fragment is expressed in frame fused with a chitin binding domain sequence, and a Pro-Gly is appended to the native C terminus of the protein of interest. The presence of a C-terminal glycine reduces the chance of side reactions, because the glycine residue accelerates native chemical ligation. Affinity chromatography with a chitin resin is used to purify the expressed fusion protein, and the chemical ligation step is initiated by incubating the resin-bound protein with thiophenol and synthetic peptide in buffer. This mixture produces the in situ generation of a highly reactive phenyl $^\alpha$thioester derivative of the protein that rapidly ligates with the synthetic peptide to produce the desired semi-synthetic protein. For a review, see Kochendoerfer and Kent, *Curr. Opin. Chem. Biol.* 3:665 (1999).

In an alternative approach, peptides and polypeptides can be produced using combinatorial chemistry to synthesize a library of analogs for all positions of the desired peptide or polypeptide. See, for example, Gershengorn et al., international publication No. WO 98/34948, Hruby et al., *Curr. Opin. Chem. Biol.* 1:114 (1997), and al-Obeidi et al., *Mol. Biotechnol.* 9:205 (1998).

5. Recombinant Production of Complement C1s Inhibitor Peptides and Polypeptides

The peptides and polypeptides of the present can also be produced in recombinant host cells following conventional techniques. Nucleic acid molecules that encode a C1s exosite binding moiety, a C1s catalytic site-directed moiety, or a bivalent inhibitor polypeptide can synthesized with "gene machines" using protocols such as the phosphoramidite method. If chemically-synthesized double stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes, however, special strategies may be required, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

To express a complement C1s inhibitor peptide or polypeptide encoding sequence, a nucleic acid molecule encoding the peptide or polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene, which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. Expression vectors can also include nucleotide sequences encoding a secretory sequence that directs the heterologous polypeptide into the secretory pathway of a host cell.

Complement C1s inhibitor peptides and polypeptides of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 [Chasin et al., *Som. Cell. Molec. Genet.* 12:555 1986]), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from viral sources, such as adenovirus, bovine papilloma virus, simian virus, or the like, in which the regulatory signals are associated with a particular gene which has a high level of expression. Suitable transcriptional and translational regulatory sequences also can be obtained from mammalian genes, such as actin, collagen, myosin, and metallothionein genes.

Transcriptional regulatory sequences include a promoter region sufficient to direct the initiation of RNA synthesis. Suitable eukaryotic promoters include the promoter of the mouse *metallothionein I* gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163–181 (John Wiley & Sons, Inc. 1996)).

Alternatively, a prokaryotic promoter, such as the bacteriophage T3 RNA polymerase promoter, can be used to control expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase, which confers resistance to methotrexate. Other drug resistance genes (e.g., hygromycin resistance, multidrug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Complement C1s inhibitor peptides and polypeptides can also be produced by cultured mammalian cells using a viral delivery system. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol.* 15:145 (1994)).

Nucleic acid molecules encoding complement C1s inhibitor peptides and polypeptides may also be expressed in other higher eukaryotic cells, such as avian, fungal, insect, yeast, or plant cells. The baculovirus system provides an efficient means to introduce cloned complement C1s inhibitor genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the complement C1s inhibitor polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed complement C1s inhibitor polypeptide, for example, a Glu-Glu epitope tag (Grussenmeyer et al., *Proc. Nat'l Acad Sci.* 82:7952 (1985)). Using a technique known in the art, a transfer vector containing a complement C1s inhibitor peptide or polypeptide encoding sequence is transformed into *E. coli*, and screened for bacmids, which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270:1543 (1995). In such transfer vector constructs, a short or long version of the basic protein promoter can be used. Moreover, transfer vectors can be constructed with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to express the C1s inhibitory peptide or polypeptide.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately $2–5\times10^5$ cells to a density of $1–2\times10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology*, Volume 7: *Gene Transfer* and *Expression Protocols*, Murray (ed.), pages 147–168 (The Humana Press, Inc. 1991), by Patel et al., "The baculovirus expression system," in *DNA Cloning 2: Expression Systems, 2nd Edition*, Glover et al. (eds.), pages 205–244 (Oxford University Press 1995), by Ausubel (1995) at pages 16–37 to 16–57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183–218 (John Wiley & Sons, Inc. 1996).

Fungal cells, including yeast cells, can also be used to express the genes described herein. Yeast species of particular interest in this regard include *Saccharomyces cerevisiae*, *Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11–23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which can be linearized prior to transformation. For polypeptide production in *P. methanolica* the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, the entire expression segment of the plasmid can be flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, host cells can be used in which both methanol utilization genes (AUG1 and AUG2) are deleted. For production of secreted proteins, host cells deficient in vacuolar protease genes (PEP4 and PRB1) can be used. Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al, "Procedures for Introducing Foreign DNA into Plants," in *Methods in Plant Molecular Biology and Biotechnology*, Glick et al. (eds.), pages 67–88 (CRC Press, 1993).

Alternatively, nucleotide sequence encoding complement C1s inhibitor peptides and polypeptides can be expressed in prokaryotic host cells. Suitable promoters that can be used to express eukaryotic polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene*, 4th Ed. (Benjamin Cummins 1987), and by Ausubel et al. (1995).

Illustrative prokaryotic hosts include *E. coli* and *Bacillus subtilus*. Suitable strains of *E. coli* include BL21(DE3), BL21(DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "Bacillus Cloning Methods," in *DNA Cloning: A Practical Approach*, Glover (ed.) (IRL Press 1985)).

When expressing a complement C1s inhibitor peptide or polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems, 2nd Edition*, Glover et al. (eds.), pages 59–92 (Oxford University Press 1995). Established methods for isolating recombinant proteins from a baculovirus system are described by Richardson (ed.), *Baculovirus Expression Protocols* (The Humana Press, Inc. 1995).

6. Isolation of Complement C1s Inhibitor Polypeptides

The peptides and polypeptides of the present invention can be purified to at least about 80% purity, to at least about 90% purity, to at least about 95% purity, or even greater than 95% purity with respect to contaminating macromolecules, particularly other proteins and nucleic acids, and free of infectious and pyrogenic agents. The peptides and polypeptides of the present invention may also be purified to a pharmaceutically pure state, which is greater than 99.9% pure. In certain preparations, a purified polypeptide is substantially free of other polypeptides, particularly other polypeptides of animal origin.

Fractionation and/or conventional purification methods can be used to obtain preparations of complement C1s inhibitor peptides and polypeptides purified from recombinant host cells. Numerous methods for purifying proteins are known in the art. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

The peptides and polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification.

Complement C1s inhibitor polypeptides or fragments thereof may be glycosylated or non-glycosylated, pegylated or non-pegylated, and may or may not include an initial methionine amino acid residue.

7. Complement C1s Inhibitor Polypeptide-Polymer Conjugates

The peptides and polypeptides of the present invention can be prepared as conjugates with various polymers. For example, such polymer can be water soluble so that the complement C1s inhibitor conjugate does not precipitate in an aqueous environment, such as a physiological environment. An example of a suitable polymer is one that has been modified to have a single reactive group, such as an active ester for acylation, or an aldehyde for alkylation, In this way, the degree of polymerization can be controlled. An example of a reactive aldehyde is polyethylene glycol propionaldehyde, or mono-($C_1$–$C_{10}$) alkoxy, or aryloxy derivatives thereof (see, for example, Harris, et al., U.S. Pat. No. 5,252,714). The polymer may be branched or unbranched. Moreover, a mixture of polymers can be used to produce complement C1s inhibitor conjugates.

Complement C1s inhibitor conjugates used for therapy can comprise pharmaceutically acceptable water-soluble polymer moieties. Suitable water-soluble polymers include polyethylene glycol (PEG), monomethoxy-PEG, mono-($C_1$–$C_{10}$)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A complement C1s inhibitor peptide or polypeptide conjugate can also comprise a mixture of such water-soluble polymers.

One example of a complement C1s inhibitor peptide or polypeptide conjugate comprises a complement C1s inhibitor moiety and a polyalkyl oxide moiety attached to the N-terminus of the complement C1s inhibitor moiety. PEG is one suitable polyalkyl oxide. As an illustration, a complement C1s inhibitor peptide or polypeptide can be modified with PEG, a process known as "PEGylation." PEGylation of peptides and polypeptides can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, complement C1s inhibitor peptide and polypeptide conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a complement C1s inhibitor peptide or polypeptide. An example of an activated PEG ester is PEG esterified to N-hydroxysuccinimide. As used herein, the term "acylation" includes the following types of linkages between a complement C1s inhibitor peptide or polypeptide and a water soluble polymer: amide, carbamate, urethane, and the like. Methods for preparing PEGylated complement C1s inhibitor peptides or polypeptides by acylation will typically comprise the steps of (a) reacting a complement C1s inhibitor moiety with PEG (such as a reactive ester of an aldehyde derivative of PEG) under conditions whereby one or more PEG groups attach to the complement C1s inhibitor moiety, and (b) obtaining the reaction product(s). Generally, the optimal reaction conditions for acylation reactions will be determined based upon known parameters and desired results. For example, the larger the ratio of PEG: complement C1s inhibitor moiety, the greater the percentage of polyPEGylated complement C1s inhibitor product.

The product of PEGylation by acylation is typically a polyPEGylated complement C1s inhibitor product, wherein the lysine ε-amino groups are PEGylated via an acyl linking group. An example of a connecting linkage is an amide. Typically, the resulting complement C1s inhibitor moiety will be at least 95% mono-, di-, or tri-pegylated, although some species with higher degrees of PEGylation may be formed depending upon the reaction conditions. PEGylated species can be separated from unconjugated complement C1s inhibitor peptides and polypeptides using standard purification methods, such as dialysis, ultrafiltration, ion exchange chromatography, affinity chromatography, and the like.

PEGylation by alkylation generally involves reacting a terminal aldehyde derivative of PEG with a complement C1s inhibitor moiety in the presence of a reducing agent. PEG groups can be attached to the polypeptide via a —$CH_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of complement C1s inhibitor monopolymer conjugates.

Reductive alkylation to produce a substantially homogenous population of monopolymer complement C1s inhibitor conjugate molecule can comprise the steps of: (a) reacting a complement C1s inhibitor peptide or polypeptide with a reactive PEG under reductive alkylation conditions at a pH suitable to permit selective modification of the α-amino group at the amino terminus of the complement C1s inhibitor moiety, and (b) obtaining the reaction product(s). The reducing agent used for reductive alkylation should be stable in aqueous solution and able to reduce only the Schiff base formed in the initial process of reductive alkylation. Illustrative reducing agents include sodium borohydride, sodium cyanoborohydride, dimethylamine borane, trimethylamine borane, and pyridine borane.

For a substantially homogenous population of monopolymer complement C1s inhibitor conjugates, the reductive alkylation reaction conditions are those which permit the selective attachment of the water soluble polymer moiety to the N-terminus of the complement C1s inhibitor moiety. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer: complement C1s inhibitor moiety need not be as large because more reactive groups are available. Typically, the pH will fall within the range of 3 to 9, or 3 to 6.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738, 846, Nieforth et al., *Clin. Pharmacol. Ther.* 59:636 (1996), Monkarsh et al., *Anal. Biochem.* 247:434 (1997)).

The present invention contemplates compositions comprising a peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

8. Therapeutic Uses of Complement C1s Inhibitor Peptides and Polypeptides

The present invention includes the use of complement C1s inhibitory peptide and polypeptides for therapy in mammals. As an illustration, these molecules can be used to treat systemic lupus erythematosus, rheumatoid arthritis, serum sickness, various hemolytic anemias, myasthenia gravis, and certain forms of nephritis. Inhibition of complement activation can also be used when tissue damage is caused by vascular injury, such as myocardial infarction, cerebral vascular accidents, reperfusion of ischemic tissue, and acute shock lung syndrome. Complement activation inhibitors are also useful for decreasing the rejection of transplanted tissues. For example, inhibition of complement can decrease vascular leak syndrome following bone marrow transplantation, or lung transplantation. The effect of vascular leak syndrome can also be decreased following open heart surgery. The complement inhibitors described herein can also be used to reduce mortality associated with the occurrence of severe thermal injury and septic shock. Additional therapeutic uses of complement inhibitors are recognized by those of skill in the art.

The present invention contemplates both veterinary and human therapeutic uses. Illustrative subjects include mammalian subjects, such as farm animals, domestic animals, and human patients.

Generally, the dosage of administered polypeptide or peptide will vary depending upon such factors as the subject's age, weight, height, sex, general medical condition and previous medical history. Typically, it is desirable to provide the recipient with a dosage of a complement C1s inhibitor peptide or polypeptide, which is in the range of from about 1 pg/kg to 10 mg/kg (amount of agent/body weight of subject), although a lower or higher dosage also may be administered as circumstances dictate.

Administration of a complement C1s inhibitor peptide or polypeptide to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255–288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising complement C1s inhibitor peptides or polypeptides can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269: 850 (1995)). Transdermal delivery using electroporation provides another means to administer complement C1s inhibitor peptides or polypeptides (Potts et al., *Pharm. Biotechnol.* 10:213 (1997)).

A pharmaceutical composition comprising a complement C1s inhibitor peptide or polypeptide can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient subject. Sterile phosphate-buffered saline is one example of a pharmaceutically acceptable carrier. Other suitable carriers are well-known to those in the art. See, for example, Gennaro (ed.), *Remington's Pharmaceutical Sciences,* 19th Edition (Mack Publishing Company 1995).

For purposes of therapy, a complement C1s inhibitor peptide or polypeptide and a pharmaceutically acceptable carrier are administered to a subject in a therapeutically effective amount. A combination of a complement C1s inhibitor peptide, or polypeptide, and a pharmaceutically acceptable carrier is said to be administered in a "therapeutically effective amount" if the amount administered is physiologically significant. An agent is physiologically significant if its presence results in a detectable change in the physiology of a recipient subject.

A pharmaceutical composition comprising a complement C1s inhibitor peptide or polypeptide can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95–123 (CRC Press 1995); Bremer et al., "Protein Delivery with Infusion Pumps," in *Protein Delivery: Physical Systems*, Sanders and Hendren (eds.), pages 239–254 (Plenum Press 1997); Yewey et al., "Delivery of Proteins from a Controlled Release Injectable Implant," in *Protein Delivery: Physical Systems*, Sanders and Hendren (eds.), pages 93–117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (*Suppl.* 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3–24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

A complement C1s inhibitor peptide or polypeptide can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology,* 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly (ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly(lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51–93 (CRC Press 1995); Roskos and Maskiewicz, "Degradable Controlled Release Systems Useful for Protein Delivery," in *Protein Delivery: Physical Systems*, Sanders and Hendren (eds.), pages 45–92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, *Drug Delivery Systems* (CRC Press 1996).

As an illustration, pharmaceutical compositions may be supplied as a kit comprising a container that comprises a complement C1s inhibitor peptide or polypeptide. Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the complement C1s inhibitor peptide or polypeptide is contraindicated in patients with known hypersensitivity to complement C1s inhibitor peptides or polypeptides.

A variety of animal models are available to examine the efficacy of particular formulations of the inhibitory peptides and polypeptides described herein. For example, animal models provide a means to test efficacy in the treatment of sepsis, pulmonary dysfunction, pancreatitis, acute myocardial infarction, lung transplantation, trauma, thermal injury, and the like (for a review, see Caliezi et al., *Pharmacol. Rev.* 52:91 (2000)).

The present invention, thus generally described, will be understood more readily by reference to the following examples, which are provided by way of illustration and are not intended to be limiting of the present invention.

EXAMPLE 1

C1s Enzyme Assay and Classical Complement Hemolysis Assay

C1s enzyme assays were performed in 96 well plates preincubated in the assay buffer for 30 minutes at room temperature. Activated human C1s (Calbiochem-Novabiochem Corporation; San Diego, Calif.); final assay concentration: 1.25 µg/ml), was incubated with samples in 50 mM Tris-HCl (pH 8) that contained 116 mM sodium chloride and 0.05% Polysorbate 80. The chromogenic substrate, Pefa-C1E (Centerchem, Inc.; Stamford, Conn.; final assay concentration: 0.4 mM), was added to the assay wells and the plate was read at 405 nm, 37° C., for 30 minutes at 20 second intervals on a SPECTRAmax PLUS plate reader (Molecular Devices Corporation; Sunnyvale, Calif.). Inhibition was determined as a decrease in Vmax, which is calculated as the maximum Δ milli-absorbance units/min over the assay period.

An assay was performed to determine the effect of BD001 on classical complement hemolysis. A pool of pre-sensitized sheep erythrocytes (DiaMedix Corporation; Miami, Fla.) was distributed into 50 milliliter conical tubes, and centrifuged at 1000 rpm for 10 minutes. Supernatants were discarded, and remaining pellets were resuspended in Gelatin Veronal buffer (Sigma Chemical Company; St. Louis, Mo.). The pellets were washed twice again with Gelatin Veronal buffer.

A standard curve of lysed cells was created by diluting cells in distilled water. The cells were resuspended in an appropriate volume to provide a 100% lysis absorbance reading of 0.7 AU at 415 nm. A serum serial dilution was performed to determine which serum dilution will provide 75% lysis; this is the serum dilution that was used for the assay. The assay was performed by incubating: 100 µl Gelatin Veronal buffer, 50 µl of a serum dilution or Gelatin Veronal buffer; 50 µl of sample or Gelatin Veronal buffer; and 50 µl of pre-sensitized rabbit erythrocytes for one hour at 37° C. After centrifuging the plate for 10 minutes at 1500 rpm, 100 µl of supernatant were transferred to a new plate. The plates were read at 415 nm on a SPECTRAmax PLUS plate reader. Inhibition was measured as a decrease in absorbance from maximum lysis.

Differences were observed in the activity of BD001 protein isolated from baculovirus and *Pichia* systems. According to the C1s enzyme assay, the IC$_{50}$ calculated for the baculovirus material was 5.2 nM, whereas the *Pichia* material provided an IC$_{50}$ of 44 nM, or about eight-fold less active than the baculovirus material.

EXAMPLE 2

Effects of Posttranslational Modification on BD001 Activity

Three types of post-translational modifications have been identified in BD001: (1) glycosylation at Asn$^{23}$ consisting of a fucosylated complex-type core; (2) sulfation of at least one of Tyr$^{117}$, Tyr$^{119}$, and Tyr$^{121}$; and (3) proteolytic cleavage after Arg$^{65}$. The first two modifications have been identified in native BD001 as well as recombinant BD001 expressed in Baculovirus. The third modification is seen in a fraction of the recombinant BD001 expressed in Baculovirus. To evaluate the effect of these posttranslational modifications on activity, sulfate groups were removed from recombinant BD001 using aryl sulfatase (Sigma Chemical Co.; St. Louis, Mo.) in 10 mM acetate, 120 mM NaCl (pH 5.5), recombinant BD001 proteins were deglycosylated using PNGase F (CALBIOCHEM-NOVABIOCHEM Corp.; La Jolla, Calif.) in buffer supplied by the manufacturer, and the cleaved recombinant BD001 species was separated from intact BD001 using reverse phase high-pressure liquid chromatography (Zorbax 300SB-C18, 10–30% ACN gradient, 60° C.). Following treatment, the proteins were lyophilized, and then reconstituted in MilliQ water. The identity of each species was verified using mass spectroscopy, and protein concentrations were measured using absorbance at 280 nm. The C1s enzyme assay, described above, was used to evaluate activity.

As shown in Table 6, removal of the glycosylation had a negligible effect on the IC$_{50}$ of recombinant BD001, whereas the removal of sulfate had a significant effect on the IC$_{50}$ of recombinant BD001. In addition, cleaved BD001 was found to have an approximate 10 fold higher IC$_{50}$ than the matched, intact form.

TABLE 6

| Protein | IC$_{50}$ (nM) |
|---|---|
| BD001 isolated from tissue | 4.0, 4.7 |
| Recombinant BD001 | 2.5 |
| Deglycosylated recombinant BD001 | 2.86 |
| Desulfated recombinant BD001 | 36 |
| Cleaved recombinant BD001 | 19.8 |

TABLE 6-continued

| Protein | IC$_{50}$ (nM) |
|---|---|
| Deglycosylated and cleaved recombinant BD001 | 21.9 |
| Desulfated and cleaved recombinant BD001 | 558 |

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A peptide or polypeptide that inhibits complement C1s, wherein the peptide or polypeptide comprises the amino acid sequence "CRLGC" (amino acid residues 64 to 68 of SEQ ID NO:1), wherein the peptide or polypeptide consists of five to thirty amino acid residues of SEQ ID NO: 1.

2. The peptide or polypeptide of claim 1, wherein the polypeptide consists of the amino acid sequence:

"GCDGFKCRLG CTYGFKTDKK GCEAFCTCNT" (SEQ ID NO:53).

3. The peptide or polypeptide of claim 1, wherein the peptide consists of the amino acid sequence: "CRLGC" (amino acid residues 64 to 68 of SEQ ID NO:1).

* * * * *

SEQUENCE LISTING

```
<160> NUMBER OF SEQ ID NOS: 140

<210> SEQ ID NO 1
<211> LENGTH: 122
<212> TYPE: PRT
<213> ORGANISM: Haementaria ghilianii

<400> SEQUENCE: 1

Ala Lys Lys Lys Leu Pro Lys Cys Gln Lys Gln Glu Asp Cys Gly Ser
 1               5                  10                  15

Trp Asp Leu Lys Cys Asn Asn Val Thr Lys Lys Cys Glu Cys Arg Asn
                20                  25                  30

Gln Val Cys Gly Arg Gly Cys Pro Lys Glu Arg Tyr Gln Arg Asp Lys
            35                  40                  45

Tyr Gly Cys Arg Lys Cys Leu Cys Lys Gly Cys Asp Gly Phe Lys Cys
        50                  55                  60

Arg Leu Gly Cys Thr Tyr Gly Phe Lys Thr Asp Lys Lys Gly Cys Glu
65                  70                  75                  80

Ala Phe Cys Thr Cys Asn Thr Lys Glu Thr Ala Cys Val Asn Ile Trp
                85                  90                  95

Cys Thr Asp Pro Tyr Lys Cys Asn Pro Glu Ser Gly Arg Cys Glu Asp
            100                 105                 110

Pro Asn Glu Glu Tyr Glu Tyr Asp Tyr Glu
        115                 120

<210> SEQ ID NO 2
<211> LENGTH: 10
<212> TYPE: PRT
<213> ORGANISM: Artificial Sequence
<220> FEATURE:
<223> OTHER INFORMATION: C1s exosite binding moiety

<400> SEQUENCE: 2

Pro Asn Glu Glu Tyr Glu Tyr Asp Tyr Glu
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
```

```
<400> SEQUENCE: 3

Pro Asn Glu Glu Xaa Glu Tyr Asp Tyr Glu
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (7)...(7)
<223> OTHER INFORMATION: Xaa = Phe-(p-CH2)SO3H

<400> SEQUENCE: 4

Pro Asn Glu Glu Tyr Glu Xaa Asp Tyr Glu
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (9)...(9)
<223> OTHER INFORMATION: Xaa = Phe-(p-CH2)SO3H

<400> SEQUENCE: 5

Pro Asn Glu Glu Tyr Glu Tyr Asp Xaa Glu
 1               5                  10

<210> SEQ ID NO 6
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (7)...(7)
<223> OTHER INFORMATION: Xaa = Phe-(p-CH2)SO3H

<400> SEQUENCE: 6

Pro Asn Glu Glu Xaa Glu Xaa Asp Tyr Glu
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (9)...(9)
<223> OTHER INFORMATION: Xaa = Phe-(p-CH2)SO3H

<400> SEQUENCE: 7

Pro Asn Glu Glu Xaa Glu Tyr Asp Xaa Glu
 1               5                  10
```

-continued

```
<210> SEQ ID NO 8
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (7)...(7)
<223> OTHER INFORMATION: Xaa = Phe-(p-CH2)SO3H
<221> NAME/KEY: MUTAGEN
<222> LOCATION: (9)...(9)
<223> OTHER INFORMATION: Xaa = Phe-(p-CH2)SO3H

<400> SEQUENCE: 8

Pro Asn Glu Glu Tyr Glu Xaa Asp Xaa Glu
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (7)...(0)
<223> OTHER INFORMATION: Xaa = Phe-(p-CH2)SO3H
<221> NAME/KEY: MUTAGEN
<222> LOCATION: (9)...(9)
<223> OTHER INFORMATION: Xaa = Phe-(p-CH2)SO3H

<400> SEQUENCE: 9

Pro Asn Glu Glu Xaa Glu Xaa Asp Xaa Glu
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine

<400> SEQUENCE: 10

Pro Asn Glu Glu Xaa Glu Tyr Asp Tyr Glu
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (7)...(7)
<223> OTHER INFORMATION: Xaa = sulfated tyrosine

<400> SEQUENCE: 11

Pro Asn Glu Glu Tyr Glu Xaa Asp Tyr Glu
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: C1s exosite binding moiety
```

```
<221> NAME/KEY: MUTAGEN
<222> LOCATION: (9)...(9)
<223> OTHER INFORMATION: Xaa = sulfated tyrosine

<400> SEQUENCE: 12

Pro Asn Glu Glu Tyr Glu Tyr Asp Xaa Glu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (7)...(7)
<223> OTHER INFORMATION: Xaa = sulfated tyrosine

<400> SEQUENCE: 13

Pro Asn Glu Glu Xaa Glu Xaa Asp Tyr Glu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (9)...(9)
<223> OTHER INFORMATION: Xaa = sulfated tyrosine

<400> SEQUENCE: 14

Pro Asn Glu Glu Xaa Glu Tyr Asp Xaa Glu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (7)...(7)
<223> OTHER INFORMATION: Xaa = sulfated tyrosine
<221> NAME/KEY: MUTAGEN
<222> LOCATION: (9)...(9)
<223> OTHER INFORMATION: Xaa = sulfated tyrosine

<400> SEQUENCE: 15

Pro Asn Glu Glu Tyr Glu Xaa Asp Xaa Glu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (7)...(7)
<223> OTHER INFORMATION: Xaa = sulfated tyrosine
```

```
<221> NAME/KEY: MUTAGEN
<222> LOCATION: (9)...(9)
<223> OTHER INFORMATION: Xaa = sulfated tyrosine

<400> SEQUENCE: 16

Pro Asn Glu Glu Xaa Glu Xaa Asp Xaa Glu
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (7)...(7)
<223> OTHER INFORMATION: Xaa = sulfated tyrosine

<400> SEQUENCE: 17

Pro Asn Glu Glu Xaa Glu Xaa Asp Tyr Glu
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (7)...(7)
<223> OTHER INFORMATION: Xaa = Phe-(p-CH2)SO3H

<400> SEQUENCE: 18

Pro Asn Glu Glu Xaa Glu Xaa Asp Tyr Glu
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (9)...(9)
<223> OTHER INFORMATION: Xaa = sulfated tyrosine

<400> SEQUENCE: 19

Pro Asn Glu Glu Xaa Glu Tyr Asp Xaa Glu
 1               5                  10

<210> SEQ ID NO 20
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (9)...(9)
<223> OTHER INFORMATION: Xaa = Phe-(p-CH2)SO3H
```

-continued

```
<400> SEQUENCE: 20

Pro Asn Glu Glu Xaa Glu Tyr Asp Xaa Glu
1               5                   10

<210> SEQ ID NO 21
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (7)...(7)
<223> OTHER INFORMATION: Xaa = Phe-(p-CH2)SO3H
<221> NAME/KEY: MUTAGEN
<222> LOCATION: (9)...(9)
<223> OTHER INFORMATION: Xaa = sulfated tyrosine

<400> SEQUENCE: 21

Pro Asn Glu Glu Tyr Glu Xaa Asp Xaa Glu
1               5                   10

<210> SEQ ID NO 22
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (7)...(7)
<223> OTHER INFORMATION: Xaa = sulfated tyrosine
<221> NAME/KEY: MUTAGEN
<222> LOCATION: (9)...(9)
<223> OTHER INFORMATION: Xaa = Phe-(p-CH2)SO3H

<400> SEQUENCE: 22

Pro Asn Glu Glu Tyr Glu Xaa Asp Xaa Glu
1               5                   10

<210> SEQ ID NO 23
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (7)...(7)
<223> OTHER INFORMATION: Xaa = Phe-(p-CH2)SO3H
<221> NAME/KEY: MUTAGEN
<222> LOCATION: (9)...(9)
<223> OTHER INFORMATION: Xaa = sulfated tyrosine

<400> SEQUENCE: 23

Pro Asn Glu Glu Xaa Glu Xaa Asp Xaa Glu
1               5                   10

<210> SEQ ID NO 24
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (7)...(7)
<223> OTHER INFORMATION: Xaa = Phe-(p-CH2)SO3H
```

```
<221> NAME/KEY: MUTAGEN
<222> LOCATION: (9)...(9)
<223> OTHER INFORMATION: Xaa = Phe-(p-CH2)SO3H

<400> SEQUENCE: 24

Pro Asn Glu Glu Xaa Glu Xaa Asp Xaa Glu
1               5                   10

<210> SEQ ID NO 25
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (7)...(7)
<223> OTHER INFORMATION: Xaa = sulfated tyrosine
<221> NAME/KEY: MUTAGEN
<222> LOCATION: (9)...(9)
<223> OTHER INFORMATION: Xaa = sulfated tyrosine

<400> SEQUENCE: 25

Pro Asn Glu Glu Xaa Glu Xaa Asp Xaa Glu
1               5                   10

<210> SEQ ID NO 26
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (7)...(7)
<223> OTHER INFORMATION: Xaa = sulfated tyrosine
<221> NAME/KEY: MUTAGEN
<222> LOCATION: (9)...(9)
<223> OTHER INFORMATION: Xaa = Phe-(p-CH2)SO3H

<400> SEQUENCE: 26

Pro Asn Glu Glu Xaa Glu Xaa Asp Xaa Glu
1               5                   10

<210> SEQ ID NO 27
<211> LENGTH: 10
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (7)...(7)
<223> OTHER INFORMATION: Xaa = sulfated tyrosine
<221> NAME/KEY: MUTAGEN
<222> LOCATION: (9)...(9)
<223> OTHER INFORMATION: Xaa = Phe-(p-CH2)SO3H

<400> SEQUENCE: 27

Pro Asn Glu Glu Xaa Glu Xaa Asp Xaa Glu
1               5                   10
```

```
<210> SEQ ID NO 28
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H

<400> SEQUENCE: 28

Ala Asn Glu Asp Xaa Glu Asp Tyr Glu Tyr Asp
 1               5                  10

<210> SEQ ID NO 29
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (8)...(8)
<223> OTHER INFORMATION: Xaa = Phe-(p-CH2)SO3H

<400> SEQUENCE: 29

Ala Asn Glu Asp Tyr Glu Asp Xaa Glu Tyr Asp
 1               5                  10

<210> SEQ ID NO 30
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (10)...(10)
<223> OTHER INFORMATION: Xaa = Phe-(p-CH2)SO3H

<400> SEQUENCE: 30

Ala Asn Glu Asp Tyr Glu Asp Tyr Glu Xaa Asp
 1               5                  10

<210> SEQ ID NO 31
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (8)...(8)
<223> OTHER INFORMATION: Xaa = Phe-(p-CH2)SO3H

<400> SEQUENCE: 31

Ala Asn Glu Asp Xaa Glu Asp Xaa Glu Tyr Asp
 1               5                  10

<210> SEQ ID NO 32
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (10)...(10)
<223> OTHER INFORMATION: Xaa = Phe-(p-CH2)SO3H
```

-continued

```
<400> SEQUENCE: 32

Ala Asn Glu Asp Xaa Glu Asp Tyr Glu Xaa Asp
1               5                   10

<210> SEQ ID NO 33
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (8)...(8)
<223> OTHER INFORMATION: Xaa = Phe-(p-CH2)SO3H
<221> NAME/KEY: MUTAGEN
<222> LOCATION: (10)...(10)
<223> OTHER INFORMATION: Xaa = Phe-(p-CH2)SO3H

<400> SEQUENCE: 33

Ala Asn Glu Asp Tyr Glu Asp Xaa Glu Xaa Asp
1               5                   10

<210> SEQ ID NO 34
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (8)...(8)
<223> OTHER INFORMATION: Xaa = Phe-(p-CH2)SO3H
<221> NAME/KEY: MUTAGEN
<222> LOCATION: (10)...(10)
<223> OTHER INFORMATION: Xaa = Phe-(p-CH2)SO3H

<400> SEQUENCE: 34

Ala Asn Glu Asp Xaa Glu Asp Xaa Glu Xaa Asp
1               5                   10

<210> SEQ ID NO 35
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine

<400> SEQUENCE: 35

Ala Asn Glu Asp Xaa Glu Asp Tyr Glu Tyr Asp
1               5                   10

<210> SEQ ID NO 36
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (8)...(8)
<223> OTHER INFORMATION: Xaa = sulfated tyrosine

<400> SEQUENCE: 36

Ala Asn Glu Asp Tyr Glu Asp Xaa Glu Tyr Asp
1               5                   10
```

<210> SEQ ID NO 37
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (10)...(10)
<223> OTHER INFORMATION: Xaa = sulfated tyrosine

<400> SEQUENCE: 37

Ala Asn Glu Asp Tyr Glu Asp Tyr Glu Xaa Asp
 1               5                  10

<210> SEQ ID NO 38
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (8)...(8)
<223> OTHER INFORMATION: Xaa = sulfated tyrosine

<400> SEQUENCE: 38

Ala Asn Glu Asp Xaa Glu Asp Xaa Glu Tyr Asp
 1               5                  10

<210> SEQ ID NO 39
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (10)...(10)
<223> OTHER INFORMATION: Xaa = sulfated tyrosine

<400> SEQUENCE: 39

Ala Asn Glu Asp Xaa Glu Asp Tyr Glu Xaa Asp
 1               5                  10

<210> SEQ ID NO 40
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (8)...(8)
<223> OTHER INFORMATION: Xaa = sulfated tyrosine
<221> NAME/KEY: MUTAGEN
<222> LOCATION: (10)...(10)
<223> OTHER INFORMATION: Xaa = sulfated tyrosine

<400> SEQUENCE: 40

Ala Asn Glu Asp Tyr Glu Asp Xaa Glu Xaa Asp
 1               5                  10

<210> SEQ ID NO 41
<211> LENGTH: 11
<212> TYPE: PRT
<213> ORGANISM: Artificial Sequence
<220> FEATURE:
<223> OTHER INFORMATION: C1s exosite binding moiety -continued

```
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (8)...(8)
<223> OTHER INFORMATION: Xaa = sulfated tyrosine
<221> NAME/KEY: MUTAGEN
<222> LOCATION: (10)...(10)
<223> OTHER INFORMATION: Xaa = sulfated tyrosine

<400> SEQUENCE: 41

Ala Asn Glu Asp Xaa Glu Asp Xaa Glu Xaa Asp
1               5                   10

<210> SEQ ID NO 42
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (8)...(8)
<223> OTHER INFORMATION: Xaa = sulfated tyrosine

<400> SEQUENCE: 42

Ala Asn Glu Asp Xaa Glu Asp Xaa Glu Tyr Asp
1               5                   10

<210> SEQ ID NO 43
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (8)...(8)
<223> OTHER INFORMATION: Xaa = Phe-(p-CH2)SO3H

<400> SEQUENCE: 43

Ala Asn Glu Asp Xaa Glu Asp Xaa Glu Tyr Asp
1               5                   10

<210> SEQ ID NO 44
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (10)...(10)
<223> OTHER INFORMATION: Xaa = sulfated tyrosine

<400> SEQUENCE: 44

Ala Asn Glu Asp Xaa Glu Asp Tyr Glu Xaa Asp
1               5                   10

<210> SEQ ID NO 45
<211> LENGTH: 11
<212> TYPE: PRT
<213> ORGANISM: Artificial Sequence
<220> FEATURE:
<223> OTHER INFORMATION: C1s exosite binding moiety
```

```
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (10)...(10)
<223> OTHER INFORMATION: Xaa = Phe-(p-CH2)SO3H

<400> SEQUENCE: 45

Ala Asn Glu Asp Xaa Glu Asp Tyr Glu Xaa Asp
 1               5                  10

<210> SEQ ID NO 46
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (8)...(8)
<223> OTHER INFORMATION: Xaa = Phe-(p-CH2)SO3H
<221> NAME/KEY: MUTAGEN
<222> LOCATION: (10)...(10)
<223> OTHER INFORMATION: Xaa = sulfated tyrosine

<400> SEQUENCE: 46

Ala Asn Glu Asp Tyr Glu Asp Xaa Glu Xaa Asp
 1               5                  10

<210> SEQ ID NO 47
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (8)...(8)
<223> OTHER INFORMATION: Xaa = sulfated tyrosine
<221> NAME/KEY: MUTAGEN
<222> LOCATION: (10)...(10)
<223> OTHER INFORMATION: Xaa = Phe-(p-CH2)SO3H

<400> SEQUENCE: 47

Ala Asn Glu Asp Tyr Glu Asp Xaa Glu Xaa Asp
 1               5                  10

<210> SEQ ID NO 48
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (8)...(8)
<223> OTHER INFORMATION: Xaa = Phe-(p-CH2)SO3H
<221> NAME/KEY: MUTAGEN
<222> LOCATION: (10)...(10)
<223> OTHER INFORMATION: Xaa = sulfated tyrosine

<400> SEQUENCE: 48

Ala Asn Glu Asp Xaa Glu Asp Xaa Glu Xaa Asp
 1               5                  10

<210> SEQ ID NO 49
<211> LENGTH: 11
<212> TYPE: PRT
<213> ORGANISM: Artificial Sequence
<220> FEATURE:
<223> OTHER INFORMATION: C1s exosite binding moiety
```

```
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (8)...(8)
<223> OTHER INFORMATION: Xaa = Phe-(p-CH2)SO3H
<221> NAME/KEY: MUTAGEN
<222> LOCATION: (10)...(10)
<223> OTHER INFORMATION: Xaa = Phe-(p-CH2)SO3H

<400> SEQUENCE: 49

Ala Asn Glu Asp Xaa Glu Asp Xaa Glu Xaa Asp
 1               5                  10

<210> SEQ ID NO 50
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (8)...(8)
<223> OTHER INFORMATION: Xaa = sulfated tyrosine
<221> NAME/KEY: MUTAGEN
<222> LOCATION: (10)...(10)
<223> OTHER INFORMATION: Xaa = sulfated tyrosine

<400> SEQUENCE: 50

Ala Asn Glu Asp Xaa Glu Asp Xaa Glu Xaa Asp
 1               5                  10

<210> SEQ ID NO 51
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = Phe-(p-CH2)SO3H
<221> NAME/KEY: MUTAGEN
<222> LOCATION: (8)...(8)
<223> OTHER INFORMATION: Xaa = sulfated tyrosine
<221> NAME/KEY: MUTAGEN
<222> LOCATION: (10)...(10)
<223> OTHER INFORMATION: Xaa = Phe-(p-CH2)SO3H

<400> SEQUENCE: 51

Ala Asn Glu Asp Xaa Glu Asp Xaa Glu Xaa Asp
 1               5                  10

<210> SEQ ID NO 52
<211> LENGTH: 11
<212> TYPE: PRT
<213> ORGANISM: Artificial Sequence
<220> FEATURE:
<223> OTHER INFORMATION: C1s exosite binding moiety
<221> NAME/KEY: MUTAGEN
<222> LOCATION: (5)...(5)
<223> OTHER INFORMATION: Xaa = sulfated tyrosine
<221> NAME/KEY: MUTAGEN
<222> LOCATION: (8)...(8)
<223> OTHER INFORMATION: Xaa = sulfated tyrosine
<221> NAME/KEY: MUTAGEN
<222> LOCATION: (10)...(10)
<223> OTHER INFORMATION: Xaa = Phe-(p-CH2)SO3H
```

```
<400> SEQUENCE: 52

Ala Asn Glu Asp Xaa Glu Asp Xaa Glu Xaa Asp
 1               5                  10

<210> SEQ ID NO 53
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 53

Gly Cys Asp Gly Phe Lys Cys Arg Leu Gly Cys Thr Tyr Gly Phe Lys
 1               5                  10                  15

Thr Asp Lys Lys Gly Cys Glu Ala Phe Cys Thr Cys Asn Thr
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 54

Gly Cys Asp Gly Phe Lys Ser Arg Leu Gly Ser Thr Tyr Gly Phe Lys
 1               5                  10                  15

Thr Asp Lys Lys Gly Cys Glu Ala Phe Ser Thr Ser Asn Thr
            20                  25                  30

<210> SEQ ID NO 55
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 55

Gly Ser Asp Gly Phe Lys Cys Arg Leu Gly Ser Thr Tyr Gly Phe Lys
 1               5                  10                  15

Thr Asp Lys Lys Gly Ser Glu Ala Phe Cys Thr Ser Asn Thr
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 56

Gly Ser Asp Gly Phe Lys Ser Arg Leu Gly Cys Thr Tyr Gly Phe Lys
 1               5                  10                  15

Thr Asp Lys Lys Gly Ser Glu Ala Phe Ser Thr Cys Asn Thr
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: C1s catalytic site-directed moiety
```

-continued

```
<400> SEQUENCE: 57

Gly Cys Asp Gly Phe Lys Ser Arg Leu Gly Thr Tyr Gly Phe Lys
 1               5                  10                  15

Thr Asp Lys Lys Gly Cys Glu Ala Phe Cys Thr Cys Asn Thr
             20                  25                  30

<210> SEQ ID NO 58
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 58

Gly Cys Asp Gly Phe Lys Cys Arg Leu Gly Ser Thr Tyr Gly Phe Lys
 1               5                  10                  15

Thr Asp Lys Lys Gly Cys Glu Ala Phe Cys Thr Cys Asn Thr
             20                  25                  30

<210> SEQ ID NO 59
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 59

Gly Cys Asp Gly Phe Lys Cys Arg Leu Gly Cys Thr Tyr Gly Phe Lys
 1               5                  10                  15

Thr Asp Lys Lys Gly Cys Glu Ala Phe Ser Thr Cys Asn Thr
             20                  25                  30

<210> SEQ ID NO 60
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 60

Gly Cys Asp Gly Phe Lys Cys Arg Leu Gly Cys Thr Tyr Gly Phe Lys
 1               5                  10                  15

Thr Asp Lys Lys Gly Cys Glu Ala Phe Cys Thr Ser Asn Thr
             20                  25                  30

<210> SEQ ID NO 61
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 61

Gly Cys Asp Gly Phe Lys Ser Arg Leu Gly Ser Thr Tyr Gly Phe Lys
 1               5                  10                  15

Thr Asp Lys Lys Gly Cys Glu Ala Phe Cys Thr Cys Asn Thr
             20                  25                  30

<210> SEQ ID NO 62
<211> LENGTH: 30
<212> TYPE: PRT
<213> ORGANISM: Artificial Sequence
<220> FEATURE:
<223> OTHER INFORMATION: C1s catalytic site-directed moiety
```

```
<400> SEQUENCE: 62

Gly Cys Asp Gly Phe Lys Ser Arg Leu Gly Cys Thr Tyr Gly Phe Lys
1               5                   10                  15

Thr Asp Lys Lys Gly Cys Glu Ala Phe Ser Thr Cys Asn Thr
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 63

Gly Cys Asp Gly Phe Lys Ser Arg Leu Gly Cys Thr Tyr Gly Phe Lys
1               5                   10                  15

Thr Asp Lys Lys Gly Cys Glu Ala Phe Cys Thr Ser Asn Thr
            20                  25                  30

<210> SEQ ID NO 64
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 64

Gly Cys Asp Gly Phe Lys Cys Arg Leu Gly Ser Thr Tyr Gly Phe Lys
1               5                   10                  15

Thr Asp Lys Lys Gly Cys Glu Ala Phe Ser Thr Cys Asn Thr
            20                  25                  30

<210> SEQ ID NO 65
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 65

Gly Cys Asp Gly Phe Lys Cys Arg Leu Gly Ser Thr Tyr Gly Phe Lys
1               5                   10                  15

Thr Asp Lys Lys Gly Cys Glu Ala Phe Cys Thr Ser Asn Thr
            20                  25                  30

<210> SEQ ID NO 66
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 66

Gly Cys Asp Gly Phe Lys Cys Arg Leu Gly Cys Thr Tyr Gly Phe Lys
1               5                   10                  15

Thr Asp Lys Lys Gly Cys Glu Ala Phe Ser Thr Ser Asn Thr
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: C1s catalytic site-directed moiety
```

-continued

```
<400> SEQUENCE: 67

Gly Cys Asp Gly Phe Lys Ser Arg Leu Gly Ser Thr Tyr Gly Phe Lys
1               5                   10                  15

Thr Asp Lys Lys Gly Cys Glu Ala Phe Ser Thr Cys Asn Thr
            20                  25                  30

<210> SEQ ID NO 68
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 68

Gly Cys Asp Gly Phe Lys Ser Arg Leu Gly Ser Thr Tyr Gly Phe Lys
1               5                   10                  15

Thr Asp Lys Lys Gly Cys Glu Ala Phe Cys Thr Ser Asn Thr
            20                  25                  30

<210> SEQ ID NO 69
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 69

Gly Cys Asp Gly Phe Lys Cys Arg Leu Gly Ser Thr Tyr Gly Phe Lys
1               5                   10                  15

Thr Asp Lys Lys Gly Cys Glu Ala Phe Ser Thr Ser Asn Thr
            20                  25                  30

<210> SEQ ID NO 70
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 70

Gly Cys Asp Gly Phe Lys Ser Arg Leu Gly Cys Thr Tyr Gly Phe Lys
1               5                   10                  15

Thr Asp Lys Lys Gly Cys Glu Ala Phe Ser Thr Ser Asn Thr
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 71

Gly Ser Asp Gly Phe Lys Cys Arg Leu Gly Cys Thr Tyr Gly Phe Lys
1               5                   10                  15

Thr Asp Lys Lys Gly Cys Glu Ala Phe Cys Thr Cys Asn Thr
            20                  25                  30

<210> SEQ ID NO 72
<211> LENGTH: 30
<212> TYPE: PRT
<213> ORGANISM: Artificial Sequence
<220> FEATURE:
<223> OTHER INFORMATION: C1s catalytic site-directed moiety
```

-continued

```
<400> SEQUENCE: 72

Gly Cys Asp Gly Phe Lys Cys Arg Leu Gly Ser Thr Tyr Gly Phe Lys
1               5                   10                  15

Thr Asp Lys Lys Gly Cys Glu Ala Phe Cys Thr Cys Asn Thr
            20                  25                  30

<210> SEQ ID NO 73
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 73

Gly Cys Asp Gly Phe Lys Cys Arg Leu Gly Cys Thr Tyr Gly Phe Lys
1               5                   10                  15

Thr Asp Lys Lys Gly Ser Glu Ala Phe Cys Thr Cys Asn Thr
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 74

Gly Cys Asp Gly Phe Lys Cys Arg Leu Gly Cys Thr Tyr Gly Phe Lys
1               5                   10                  15

Thr Asp Lys Lys Gly Cys Glu Ala Phe Cys Thr Ser Asn Thr
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 75

Gly Ser Asp Gly Phe Lys Cys Arg Leu Gly Ser Thr Tyr Gly Phe Lys
1               5                   10                  15

Thr Asp Lys Lys Gly Cys Glu Ala Phe Cys Thr Cys Asn Thr
            20                  25                  30

<210> SEQ ID NO 76
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 76

Gly Ser Asp Gly Phe Lys Cys Arg Leu Gly Cys Thr Tyr Gly Phe Lys
1               5                   10                  15

Thr Asp Lys Lys Gly Ser Glu Ala Phe Cys Thr Cys Asn Thr
            20                  25                  30

<210> SEQ ID NO 77
<211> LENGTH: 30
<212> TYPE: PRT
<213> ORGANISM: Artificial Sequence
<220> FEATURE:
<223> OTHER INFORMATION: C1s catalytic site-directed moiety
```

-continued

```
<400> SEQUENCE: 77

Gly Ser Asp Gly Phe Lys Cys Arg Leu Gly Cys Thr Tyr Gly Phe Lys
1               5                   10                  15

Thr Asp Lys Lys Gly Cys Glu Ala Phe Cys Thr Ser Asn Thr
            20                  25                  30

<210> SEQ ID NO 78
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 78

Gly Cys Asp Gly Phe Lys Cys Arg Leu Gly Ser Thr Tyr Gly Phe Lys
1               5                   10                  15

Thr Asp Lys Lys Gly Ser Glu Ala Phe Cys Thr Cys Asn Thr
            20                  25                  30

<210> SEQ ID NO 79
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 79

Gly Cys Asp Gly Phe Lys Cys Arg Leu Gly Ser Thr Tyr Gly Phe Lys
1               5                   10                  15

Thr Asp Lys Lys Gly Cys Glu Ala Phe Cys Thr Ser Asn Thr
            20                  25                  30

<210> SEQ ID NO 80
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 80

Gly Cys Asp Gly Phe Lys Cys Arg Leu Gly Cys Thr Tyr Gly Phe Lys
1               5                   10                  15

Thr Asp Lys Lys Gly Ser Glu Ala Phe Cys Thr Ser Asn Thr
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 81

Gly Ser Asp Gly Phe Lys Cys Arg Leu Gly Ser Thr Tyr Gly Phe Lys
1               5                   10                  15

Thr Asp Lys Lys Gly Ser Glu Ala Phe Cys Thr Cys Asn Thr
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: C1s catalytic site-directed moiety
```

```
<400> SEQUENCE: 82

Gly Ser Asp Gly Phe Lys Cys Arg Leu Gly Cys Thr Tyr Gly Phe Lys
1               5                   10                  15

Thr Asp Lys Lys Gly Ser Glu Ala Phe Cys Thr Ser Asn Thr
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 83

Gly Cys Asp Gly Phe Lys Cys Arg Leu Gly Ser Thr Tyr Gly Phe Lys
1               5                   10                  15

Thr Asp Lys Lys Gly Ser Glu Ala Phe Cys Thr Ser Asn Thr
            20                  25                  30

<210> SEQ ID NO 84
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 84

Gly Ser Asp Gly Phe Lys Cys Arg Leu Gly Ser Thr Tyr Gly Phe Lys
1               5                   10                  15

Thr Asp Lys Lys Gly Cys Glu Ala Phe Cys Thr Ser Asn Thr
            20                  25                  30

<210> SEQ ID NO 85
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 85

Gly Ser Asp Gly Phe Lys Cys Arg Leu Gly Cys Thr Tyr Gly Phe Lys
1               5                   10                  15

Thr Asp Lys Lys Gly Cys Glu Ala Phe Cys Thr Cys Asn Thr
            20                  25                  30

<210> SEQ ID NO 86
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 86

Gly Cys Asp Gly Phe Lys Ser Arg Leu Gly Cys Thr Tyr Gly Phe Lys
1               5                   10                  15

Thr Asp Lys Lys Gly Cys Glu Ala Phe Cys Thr Cys Asn Thr
            20                  25                  30

<210> SEQ ID NO 87
<211> LENGTH: 30
<212> TYPE: PRT
<213> ORGANISM: Artificial Sequence
<220> FEATURE:
<223> OTHER INFORMATION: C1s catalytic site-directed moiety
```

```
<400> SEQUENCE: 87

Gly Cys Asp Gly Phe Lys Cys Arg Leu Gly Cys Thr Tyr Gly Phe Lys
1               5                   10                  15

Thr Asp Lys Lys Gly Ser Glu Ala Phe Cys Thr Cys Asn Thr
            20                  25                  30

<210> SEQ ID NO 88
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 88

Gly Cys Asp Gly Phe Lys Cys Arg Leu Gly Cys Thr Tyr Gly Phe Lys
1               5                   10                  15

Thr Asp Lys Lys Gly Cys Glu Ala Phe Ser Thr Cys Asn Thr
            20                  25                  30

<210> SEQ ID NO 89
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 89

Gly Ser Asp Gly Phe Lys Ser Arg Leu Gly Cys Thr Tyr Gly Phe Lys
1               5                   10                  15

Thr Asp Lys Lys Gly Cys Glu Ala Phe Cys Thr Cys Asn Thr
            20                  25                  30

<210> SEQ ID NO 90
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 90

Gly Ser Asp Gly Phe Lys Cys Arg Leu Gly Cys Thr Tyr Gly Phe Lys
1               5                   10                  15

Thr Asp Lys Lys Gly Ser Glu Ala Phe Cys Thr Cys Asn Thr
            20                  25                  30

<210> SEQ ID NO 91
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 91

Gly Ser Asp Gly Phe Lys Cys Arg Leu Gly Cys Thr Tyr Gly Phe Lys
1               5                   10                  15

Thr Asp Lys Lys Gly Cys Glu Ala Phe Ser Thr Cys Asn Thr
            20                  25                  30

<210> SEQ ID NO 92
<211> LENGTH: 30
<212> TYPE: PRT
<213> ORGANISM: Artificial Sequence
<220> FEATURE:
<223> OTHER INFORMATION: C1s catalytic site-directed moiety
```

```
<400> SEQUENCE: 92

Gly Cys Asp Gly Phe Lys Ser Arg Leu Gly Cys Thr Tyr Gly Phe Lys
1               5                   10                  15

Thr Asp Lys Lys Gly Ser Glu Ala Phe Cys Thr Cys Asn Thr
            20                  25                  30

<210> SEQ ID NO 93
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 93

Gly Cys Asp Gly Phe Lys Ser Arg Leu Gly Cys Thr Tyr Gly Phe Lys
1               5                   10                  15

Thr Asp Lys Lys Gly Cys Glu Ala Phe Ser Thr Cys Asn Thr
            20                  25                  30

<210> SEQ ID NO 94
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 94

Gly Cys Asp Gly Phe Lys Cys Arg Leu Gly Cys Thr Tyr Gly Phe Lys
1               5                   10                  15

Thr Asp Lys Lys Gly Ser Glu Ala Phe Ser Thr Cys Asn Thr
            20                  25                  30

<210> SEQ ID NO 95
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 95

Gly Ser Asp Gly Phe Lys Ser Arg Leu Gly Cys Thr Tyr Gly Phe Lys
1               5                   10                  15

Thr Asp Lys Lys Gly Ser Glu Ala Phe Cys Thr Cys Asn Thr
            20                  25                  30

<210> SEQ ID NO 96
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 96

Gly Ser Asp Gly Phe Lys Ser Arg Leu Gly Cys Thr Tyr Gly Phe Lys
1               5                   10                  15

Thr Asp Lys Lys Gly Cys Glu Ala Phe Ser Thr Cys Asn Thr
            20                  25                  30

<210> SEQ ID NO 97
<211> LENGTH: 30
<212> TYPE: PRT
<213> ORGANISM: Artificial Sequence
<220> FEATURE:
<223> OTHER INFORMATION: C1s catalytic site-directed moiety
```

```
<400> SEQUENCE: 97

Gly Cys Asp Gly Phe Lys Ser Arg Leu Gly Cys Thr Tyr Gly Phe Lys
1               5                   10                  15

Thr Asp Lys Lys Gly Ser Glu Ala Phe Ser Thr Cys Asn Thr
            20                  25                  30

<210> SEQ ID NO 98
<211> LENGTH: 30
<212> TYPE: PRT
<213> ORGANISM: Artificial Sequence
<220> FEATURE:
<223> OTHER INFORMATION: C1s catalytic site-directed moiety

<400> SEQUENCE: 98

Gly Ser Asp Gly Phe Lys Cys Arg Leu Gly Cys Thr Tyr Gly Phe Lys
1               5                   10                  15

Thr Asp Lys Lys Gly Ser Glu Ala Phe Ser Thr Cys Asn Thr
            20                  25                  30

<210> SEQ ID NO 99
<211> LENGTH: 6
<212> TYPE: PRT
<213> ORGANISM: Artificial Sequence
<220> FEATURE:
<223> OTHER INFORMATION: C1s catalytic site-directed moiety

<400> SEQUENCE: 99

Cys Arg Leu Gly Cys Thr
1               5

<210> SEQ ID NO 100
<211> LENGTH: 7
<212> TYPE: PRT
<213> ORGANISM: Artificial Sequence
<220> FEATURE:
<223> OTHER INFORMATION: C1s catalytic site-directed moiety

<400> SEQUENCE: 100

Cys Arg Leu Gly Cys Thr Tyr
1               5

<210> SEQ ID NO 101
<211> LENGTH: 8
<212> TYPE: PRT
<213> ORGANISM: Artificial Sequence
<220> FEATURE:
<223> OTHER INFORMATION: C1s catalytic site-directed moiety

<400> SEQUENCE: 101

Cys Arg Leu Gly Cys Thr Tyr Gly
1               5

<210> SEQ ID NO 102
<211> LENGTH: 9
<212> TYPE: PRT
<213> ORGANISM: Artificial Sequence
<220> FEATURE:
<223> OTHER INFORMATION: C1s catalytic site-directed moiety

<400> SEQUENCE: 102

Cys Arg Leu Gly Cys Thr Tyr Gly Phe
1               5
```

<210> SEQ ID NO 103
<211> LENGTH: 10
<212> TYPE: PRT
<213> ORGANISM: Artificial Sequence
<220> FEATURE:
<223> OTHER INFORMATION: C1s catalytic site-directed moiety

<400> SEQUENCE: 103

Cys Arg Leu Gly Cys Thr Tyr Gly Phe Lys
1               5                   10

<210> SEQ ID NO 104
<211> LENGTH: 11
<212> TYPE: PRT
<213> ORGANISM: Artificial Sequence
<220> FEATURE:
<223> OTHER INFORMATION: C1s catalytic site-directed moiety

<400> SEQUENCE: 104

Cys Arg Leu Gly Cys Thr Tyr Gly Phe Lys Thr
1               5                   10

<210> SEQ ID NO 105
<211> LENGTH: 12
<212> TYPE: PRT
<213> ORGANISM: Artificial Sequence
<220> FEATURE:
<223> OTHER INFORMATION: C1s catalytic site-directed moiety

<400> SEQUENCE: 105

Cys Arg Leu Gly Cys Thr Tyr Gly Phe Lys Thr Asp
1               5                   10

<210> SEQ ID NO 106
<211> LENGTH: 13
<212> TYPE: PRT
<213> ORGANISM: Artificial Sequence
<220> FEATURE:
<223> OTHER INFORMATION: C1s catalytic site-directed moiety

<400> SEQUENCE: 106

Cys Arg Leu Gly Cys Thr Tyr Gly Phe Lys Thr Asp Lys
1               5                   10

<210> SEQ ID NO 107
<211> LENGTH: 14
<212> TYPE: PRT
<213> ORGANISM: Artificial Sequence
<220> FEATURE:
<223> OTHER INFORMATION: C1s catalytic site-directed moiety

<400> SEQUENCE: 107

Cys Arg Leu Gly Cys Thr Tyr Gly Phe Lys Thr Asp Lys Lys
1               5                   10

<210> SEQ ID NO 108
<211> LENGTH: 15
<212> TYPE: PRT
<213> ORGANISM: Artificial Sequence
<220> FEATURE:
<223> OTHER INFORMATION: C1s catalytic site-directed moiety

<400> SEQUENCE: 108

Cys Arg Leu Gly Cys Thr Tyr Gly Phe Lys Thr Asp Lys Lys Gly
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: C1s catalytic site-directed moiety

<400> SEQUENCE: 109

Cys Arg Leu Gly Cys Thr Tyr Gly Phe Lys Thr Asp Lys Lys Gly Cys
 1               5                  10                  15

<210> SEQ ID NO 110
<211> LENGTH: 17
<212> TYPE: PRT
<213> ORGANISM: Artificial Sequence
<220> FEATURE:
<223> OTHER INFORMATION: C1s catalytic site-directed moiety

<400> SEQUENCE: 110

Cys Arg Leu Gly Cys Thr Tyr Gly Phe Lys Thr Asp Lys Lys Gly Cys
 1               5                  10                  15

Glu

<210> SEQ ID NO 111
<211> LENGTH: 18
<212> TYPE: PRT
<213> ORGANISM: Artificial Sequence
<220> FEATURE:
<223> OTHER INFORMATION: C1s catalytic site-directed moiety

<400> SEQUENCE: 111

Cys Arg Leu Gly Cys Thr Tyr Gly Phe Lys Thr Asp Lys Lys Gly Cys
 1               5                  10                  15

Glu Ala

<210> SEQ ID NO 112
<211> LENGTH: 19
<212> TYPE: PRT
<213> ORGANISM: Artificial Sequence
<220> FEATURE:
<223> OTHER INFORMATION: C1s catalytic site-directed moiety

<400> SEQUENCE: 112

Cys Arg Leu Gly Cys Thr Tyr Gly Phe Lys Thr Asp Lys Lys Gly Cys
 1               5                  10                  15

Glu Ala Phe

<210> SEQ ID NO 113
<211> LENGTH: 20
<212> TYPE: PRT
<213> ORGANISM: Artificial Sequence
<220> FEATURE:
<223> OTHER INFORMATION: C1s catalytic site-directed moiety

<400> SEQUENCE: 113

Cys Arg Leu Gly Cys Thr Tyr Gly Phe Lys Thr Asp Lys Lys Gly Cys
 1               5                  10                  15

Glu Ala Phe Cys
             20

<210> SEQ ID NO 114
<211> LENGTH: 21
<212> TYPE: PRT
<213> ORGANISM: Artificial Sequence

```
<220> FEATURE:
<223> OTHER INFORMATION: C1s catalytic site-directed moiety

<400> SEQUENCE: 114

Cys Arg Leu Gly Cys Thr Tyr Gly Phe Lys Thr Asp Lys Lys Gly Cys
1               5                   10                  15

Glu Ala Phe Cys Thr
            20

<210> SEQ ID NO 115
<211> LENGTH: 22
<212> TYPE: PRT
<213> ORGANISM: Artificial Sequence
<220> FEATURE:
<223> OTHER INFORMATION: C1s catalytic site-directed moiety

<400> SEQUENCE: 115

Cys Arg Leu Gly Cys Thr Tyr Gly Phe Lys Thr Asp Lys Lys Gly Cys
1               5                   10                  15

Glu Ala Phe Cys Thr Cys
            20

<210> SEQ ID NO 116
<211> LENGTH: 23
<212> TYPE: PRT
<213> ORGANISM: Artificial Sequence
<220> FEATURE:
<223> OTHER INFORMATION: C1s catalytic site-directed moiety

<400> SEQUENCE: 116

Cys Arg Leu Gly Cys Thr Tyr Gly Phe Lys Thr Asp Lys Lys Gly Cys
1               5                   10                  15

Glu Ala Phe Cys Thr Cys Asn
            20

<210> SEQ ID NO 117
<211> LENGTH: 6
<212> TYPE: PRT
<213> ORGANISM: Artificial Sequence
<220> FEATURE:
<223> OTHER INFORMATION: C1s catalytic site-directed moiety

<400> SEQUENCE: 117

Leu Gln Arg Ala Leu Glu
1               5

<210> SEQ ID NO 118
<211> LENGTH: 24
<212> TYPE: PRT
<213> ORGANISM: Artificial Sequence
<220> FEATURE:
<223> OTHER INFORMATION: C1s catalytic site-directed moiety

<400> SEQUENCE: 118

Leu Gln Arg Ala Leu Glu Ile Leu Pro Asn Arg Val Thr Ile Lys Ala
1               5                   10                  15

Asn Arg Pro Phe Leu Val Phe Ile
            20

<210> SEQ ID NO 119
<211> LENGTH: 10
<212> TYPE: PRT
<213> ORGANISM: Artificial Sequence
<220> FEATURE:
<223> OTHER INFORMATION: C1s exosite binding moiety
```

```
<400> SEQUENCE: 119

Asn Glu Asp Tyr Glu Asp Tyr Glu Tyr Asp
1               5                   10

<210> SEQ ID NO 120
<211> LENGTH: 23
<212> TYPE: PRT
<213> ORGANISM: Artificial Sequence
<220> FEATURE:
<223> OTHER INFORMATION: Polypeptide  linker

<400> SEQUENCE: 120

Lys Glu Thr Ala Cys Val Asn Ile Trp Cys Thr Asp Pro Tyr Lys Cys
1               5                   10                  15

Asn Pro Glu Ser Gly Arg Cys
            20

<210> SEQ ID NO 121
<211> LENGTH: 29
<212> TYPE: PRT
<213> ORGANISM: Artificial Sequence
<220> FEATURE:
<223> OTHER INFORMATION: C1s catalytic site-directed moiety

<400> SEQUENCE: 121

Cys Asp Gly Phe Lys Cys Arg Leu Gly Cys Thr Tyr Gly Phe Lys Thr
1               5                   10                  15

Asp Lys Lys Gly Cys Glu Ala Phe Cys Thr Cys Asn Thr
            20                  25

<210> SEQ ID NO 122
<211> LENGTH: 4
<212> TYPE: PRT
<213> ORGANISM: Artificial Sequence
<220> FEATURE:
<223> OTHER INFORMATION: Peptide linker
<221> NAME/KEY: VARIANT
<222> LOCATION: (3)...(3)
<223> OTHER INFORMATION: Xaa = E or D
<221> NAME/KEY: VARIANT
<222> LOCATION: (4)...(4)
<223> OTHER INFORMATION: Xaa = E or D

<400> SEQUENCE: 122

Ala Leu Xaa Xaa
1

<210> SEQ ID NO 123
<211> LENGTH: 25
<212> TYPE: PRT
<213> ORGANISM: Artificial Sequence
<220> FEATURE:
<223> OTHER INFORMATION: Polypeptide linker

<400> SEQUENCE: 123

Lys Glu Thr Ala Cys Val Asn Ile Trp Cys Thr Asp Pro Tyr Lys Cys
1               5                   10                  15

Asn Pro Glu Ser Gly Arg Cys Glu Asp
            20                  25

<210> SEQ ID NO 124
<211> LENGTH: 5
<212> TYPE: PRT
<213> ORGANISM: Artificial Sequence
<220> FEATURE:
<223> OTHER INFORMATION: Peptide linker
```

```
<221> NAME/KEY: VARIANT
<222> LOCATION: (3)...(3)
<223> OTHER INFORMATION: Xaa = E or D
<221> NAME/KEY: VARIANT
<222> LOCATION: (4)...(4)
<223> OTHER INFORMATION: Xaa = E or D

<400> SEQUENCE: 124

Ala Leu Xaa Xaa Cys
 1               5

<210> SEQ ID NO 125
<211> LENGTH: 10
<212> TYPE: PRT
<213> ORGANISM: Artificial Sequence
<220> FEATURE:
<223> OTHER INFORMATION: Complement C1s inhibitor

<400> SEQUENCE: 125

Pro Asn Glu Glu Tyr Glu Tyr Glu Tyr Glu
 1               5                  10

<210> SEQ ID NO 126
<211> LENGTH: 21
<212> TYPE: PRT
<213> ORGANISM: Artificial Sequence
<220> FEATURE:
<223> OTHER INFORMATION: Formula of a complement C1s inhibitor
<221> NAME/KEY: VARIANT
<222> LOCATION: (1)...(1)
<223> OTHER INFORMATION: Xaa = A or P
<221> NAME/KEY: VARIANT
<222> LOCATION: (3)...(3)
<223> OTHER INFORMATION: Xaa = D or E
<221> NAME/KEY: VARIANT
<222> LOCATION: (4)...(4)
<223> OTHER INFORMATION: Xaa = D or E
<221> NAME/KEY: MUTAGEN
<222> LOCATION: (6)...(6)
<223> OTHER INFORMATION: Xaa = Phe-(p-CH2)SO3H
<221> NAME/KEY: MUTAGEN
<222> LOCATION: (7)...(7)
<223> OTHER INFORMATION: Xaa = sulfated tyrosine
<221> NAME/KEY: MUTAGEN
<222> LOCATION: (8)...(8)
<223> OTHER INFORMATION: Xaa = 2-sulfotyrosine
<221> NAME/KEY: VARIANT
<222> LOCATION: (9)...(9)
<223> OTHER INFORMATION: Xaa = D or E
<221> NAME/KEY: VARIANT
<222> LOCATION: (10)...(10)
<223> OTHER INFORMATION: Xaa = D or E
<221> NAME/KEY: MUTAGEN
<222> LOCATION: (12)...(12)
<223> OTHER INFORMATION: Xaa = Phe-(p-CH2)SO3H
<221> NAME/KEY: MUTAGEN
<222> LOCATION: (13)...(13)
<223> OTHER INFORMATION: Xaa = sulfated tyrosine
<221> NAME/KEY: MUTAGEN
<222> LOCATION: (14)...(14)
<223> OTHER INFORMATION: Xaa = 2-sulfotyrosine
<221> NAME/KEY: VARIANT
<222> LOCATION: (15)...(15)
<223> OTHER INFORMATION: Xaa = D or E
<221> NAME/KEY: MUTAGEN
<222> LOCATION: (17)...(17)
<223> OTHER INFORMATION: Xaa = Phe-(p-CH2)SO3H
<221> NAME/KEY: MUTAGEN
<222> LOCATION: (18)...(18)
<223> OTHER INFORMATION: Xaa = sulfated tyrosine
<221> NAME/KEY: MUTAGEN
<222> LOCATION: (19)...(19)
<223> OTHER INFORMATION: Xaa = 2-sulfotyrosine
```

```
<221> NAME/KEY: VARIANT
<222> LOCATION: (20)...(20)
<223> OTHER INFORMATION: Xaa = D or E
<221> NAME/KEY: VARIANT
<222> LOCATION: (21)...(21)
<223> OTHER INFORMATION: Xaa = D or E, or is absent

<400> SEQUENCE: 126

Xaa Asn Xaa Xaa Tyr Xaa Xaa Xaa Xaa Xaa Tyr Xaa Xaa Xaa Xaa Tyr
 1               5                  10                 15

Xaa Xaa Xaa Xaa Xaa
        20

<210> SEQ ID NO 127
<211> LENGTH: 21
<212> TYPE: PRT
<213> ORGANISM: Artificial Sequence
<220> FEATURE:
<223> OTHER INFORMATION: Complement C1s inhibitor
<221> NAME/KEY: VARIANT
<222> LOCATION: (3)...(3)
<223> OTHER INFORMATION: Xaa = D or E
<221> NAME/KEY: VARIANT
<222> LOCATION: (4)...(4)
<223> OTHER INFORMATION: Xaa = D or E
<221> NAME/KEY: MUTAGEN
<222> LOCATION: (6)...(6)
<223> OTHER INFORMATION: Xaa = Phe-(p-CH2)SO3H
<221> NAME/KEY: MUTAGEN
<222> LOCATION: (7)...(7)
<223> OTHER INFORMATION: Xaa = sulfated tyrosine
<221> NAME/KEY: MUTAGEN
<222> LOCATION: (8)...(8)
<223> OTHER INFORMATION: Xaa = 2-sulfotyrosine
<221> NAME/KEY: VARIANT
<222> LOCATION: (9)...(9)
<223> OTHER INFORMATION: Xaa = D or E
<221> NAME/KEY: VARIANT
<222> LOCATION: (10)...(10)
<223> OTHER INFORMATION: Xaa = D or E
<221> NAME/KEY: MUTAGEN
<222> LOCATION: (12)...(12)
<223> OTHER INFORMATION: Xaa = Phe-(p-CH2)SO3H
<221> NAME/KEY: MUTAGEN
<222> LOCATION: (13)...(13)
<223> OTHER INFORMATION: Xaa = sulfated tyrosine
<221> NAME/KEY: MUTAGEN
<222> LOCATION: (14)...(14)
<223> OTHER INFORMATION: Xaa = 2-sulfotyrosine
<221> NAME/KEY: VARIANT
<222> LOCATION: (15)...(15)
<223> OTHER INFORMATION: Xaa = D or E
<221> NAME/KEY: MUTAGEN
<222> LOCATION: (17)...(17)
<223> OTHER INFORMATION: Xaa = Phe-(p-CH2)SO3H
<221> NAME/KEY: MUTAGEN
<222> LOCATION: (18)...(18)
<223> OTHER INFORMATION: Xaa = sulfated tyrosine
<221> NAME/KEY: MUTAGEN
<222> LOCATION: (19)...(19)
<223> OTHER INFORMATION: Xaa = 2-sulfotyrosine
<221> NAME/KEY: VARIANT
<222> LOCATION: (20)...(20)
<223> OTHER INFORMATION: Xaa = D or E
<221> NAME/KEY: VARIANT
<222> LOCATION: (21)...(21)
<223> OTHER INFORMATION: Xaa = D or E, or is absent

<400> SEQUENCE: 127

Pro Asn Xaa Xaa Tyr Xaa Xaa Xaa Xaa Xaa Tyr Xaa Xaa Xaa Xaa Tyr
 1               5                  10                 15

Xaa Xaa Xaa Xaa Xaa
        20
```

```
<210> SEQ ID NO 128
<211> LENGTH: 21
<212> TYPE: PRT
<213> ORGANISM: Artificial Sequence
<220> FEATURE:
<223> OTHER INFORMATION: Formula of a C1s exosite binding moiety
<221> NAME/KEY: VARIANT
<222> LOCATION: (3)...(3)
<223> OTHER INFORMATION: Xaa = D or E
<221> NAME/KEY: VARIANT
<222> LOCATION: (4)...(4)
<223> OTHER INFORMATION: Xaa = D or E
<221> NAME/KEY: MUTAGEN
<222> LOCATION: (6)...(6)
<223> OTHER INFORMATION: Xaa = Phe-(p-CH2)SO3H
<221> NAME/KEY: MUTAGEN
<222> LOCATION: (7)...(7)
<223> OTHER INFORMATION: Xaa = sulfated tyrosine
<221> NAME/KEY: MUTAGEN
<222> LOCATION: (8)...(8)
<223> OTHER INFORMATION: Xaa = 2-sulfotyrosine
<221> NAME/KEY: VARIANT
<222> LOCATION: (9)...(9)
<223> OTHER INFORMATION: Xaa = D or E
<221> NAME/KEY: VARIANT
<222> LOCATION: (10)...(10)
<223> OTHER INFORMATION: Xaa = D or E
<221> NAME/KEY: MUTAGEN
<222> LOCATION: (12)...(12)
<223> OTHER INFORMATION: Xaa = Phe-(p-CH2)SO3H
<221> NAME/KEY: MUTAGEN
<222> LOCATION: (13)...(13)
<223> OTHER INFORMATION: Xaa = sulfated tyrosine
<221> NAME/KEY: MUTAGEN
<222> LOCATION: (14)...(14)
<223> OTHER INFORMATION: Xaa = 2-sulfotyrosine
<221> NAME/KEY: VARIANT
<222> LOCATION: (15)...(15)
<223> OTHER INFORMATION: Xaa = D or E
<221> NAME/KEY: MUTAGEN
<222> LOCATION: (17)...(17)
<223> OTHER INFORMATION: Xaa = Phe-(p-CH2)SO3H
<221> NAME/KEY: MUTAGEN
<222> LOCATION: (18)...(18)
<223> OTHER INFORMATION: Xaa = sulfated tyrosine
<221> NAME/KEY: MUTAGEN
<222> LOCATION: (19)...(19)
<223> OTHER INFORMATION: Xaa = 2-sulfotyrosine
<221> NAME/KEY: VARIANT
<222> LOCATION: (20)...(20)
<223> OTHER INFORMATION: Xaa = D or E
<221> NAME/KEY: VARIANT
<222> LOCATION: (21)...(21)
<223> OTHER INFORMATION: Xaa = D or E, or is absent

<400> SEQUENCE: 128

Ala Asn Xaa Xaa Tyr Xaa Xaa Xaa Xaa Xaa Tyr Xaa Xaa Xaa Xaa Tyr
 1               5                   10                  15

Xaa Xaa Xaa Xaa Xaa
            20

<210> SEQ ID NO 129
<211> LENGTH: 20
<212> TYPE: PRT
<213> ORGANISM: Artificial Sequence
<220> FEATURE:
<223> OTHER INFORMATION: Formula of a complement C1s inhibitor
<221> NAME/KEY: VARIANT
<222> LOCATION: (3)...(3)
<223> OTHER INFORMATION: Xaa = D or E
<221> NAME/KEY: VARIANT
<222> LOCATION: (4)...(4)
<223> OTHER INFORMATION: Xaa = D or E
<221> NAME/KEY: MUTAGEN
<222> LOCATION: (6)...(6)
<223> OTHER INFORMATION: Xaa = Phe-(p-CH2)SO3H
```

-continued

```
<221> NAME/KEY: MUTAGEN
<222> LOCATION: (7)...(7)
<223> OTHER INFORMATION: Xaa = sulfated tyrosine
<221> NAME/KEY: MUTAGEN
<222> LOCATION: (8)...(8)
<223> OTHER INFORMATION: Xaa = 2-sulfotyrosine
<221> NAME/KEY: VARIANT
<222> LOCATION: (9)...(9)
<223> OTHER INFORMATION: Xaa = D or E
<221> NAME/KEY: VARIANT
<222> LOCATION: (10)...(10)
<223> OTHER INFORMATION: Xaa = D or E
<221> NAME/KEY: MUTAGEN
<222> LOCATION: (12)...(12)
<223> OTHER INFORMATION: Xaa = Phe-(p-CH2)SO3H
<221> NAME/KEY: MUTAGEN
<222> LOCATION: (13)...(13)
<223> OTHER INFORMATION: Xaa = sulfated tyrosine
<221> NAME/KEY: MUTAGEN
<222> LOCATION: (14)...(14)
<223> OTHER INFORMATION: Xaa = 2-sulfotyrosine
<221> NAME/KEY: VARIANT
<222> LOCATION: (15)...(15)
<223> OTHER INFORMATION: Xaa = D or E
<221> NAME/KEY: MUTAGEN
<222> LOCATION: (17)...(17)
<223> OTHER INFORMATION: Xaa = Phe-(p-CH2)SO3H
<221> NAME/KEY: MUTAGEN
<222> LOCATION: (18)...(18)
<223> OTHER INFORMATION: Xaa = sulfated tyrosine
<221> NAME/KEY: MUTAGEN
<222> LOCATION: (19)...(19)
<223> OTHER INFORMATION: Xaa = 2-sulfotyrosine
<221> NAME/KEY: VARIANT
<222> LOCATION: (20)...(20)
<223> OTHER INFORMATION: Xaa = D or E

<400> SEQUENCE: 129

Pro Asn Xaa Xaa Tyr Xaa Xaa Xaa Xaa Xaa Tyr Xaa Xaa Xaa Xaa Tyr
1               5                   10                  15

Xaa Xaa Xaa Xaa
            20

<210> SEQ ID NO 130
<211> LENGTH: 19
<212> TYPE: PRT
<213> ORGANISM: Artificial Sequence
<220> FEATURE:
<223> OTHER INFORMATION: Formula of a complement C1s inhibitor.
<221> NAME/KEY: MUTAGEN
<222> LOCATION: (6)...(6)
<223> OTHER INFORMATION: Xaa = Phe-(p-CH2)SO3H
<221> NAME/KEY: MUTAGEN
<222> LOCATION: (7)...(7)
<223> OTHER INFORMATION: Xaa = sulfated tyrosine
<221> NAME/KEY: MUTAGEN
<222> LOCATION: (8)...(8)
<223> OTHER INFORMATION: Xaa = 2-sulfotyrosine
<221> NAME/KEY: MUTAGEN
<222> LOCATION: (11)...(11)
<223> OTHER INFORMATION: Xaa = Phe-(p-CH2)SO3H
<221> NAME/KEY: MUTAGEN
<222> LOCATION: (12)...(12)
<223> OTHER INFORMATION: Xaa = sulfated tyrosine
<221> NAME/KEY: MUTAGEN
<222> LOCATION: (13)...(13)
<223> OTHER INFORMATION: Xaa = 2-sulfotyrosine
<221> NAME/KEY: MUTAGEN
<222> LOCATION: (16)...(16)
<223> OTHER INFORMATION: Xaa = Phe-(p-CH2)SO3H
<221> NAME/KEY: MUTAGEN
<222> LOCATION: (17)...(17)
<223> OTHER INFORMATION: : Xaa = sulfated tyrosine
<221> NAME/KEY: MUTAGEN
<222> LOCATION: (18)...(18)
<223> OTHER INFORMATION: Xaa = 2-sulfotyrosine
```

```
<400> SEQUENCE: 130

Pro Asn Glu Glu Tyr Xaa Xaa Xaa Glu Tyr Xaa Xaa Xaa Glu Tyr Xaa
1               5                   10                  15

Xaa Xaa Glu

<210> SEQ ID NO 131
<211> LENGTH: 7
<212> TYPE: PRT
<213> ORGANISM: Artificial Sequence
<220> FEATURE:
<223> OTHER INFORMATION: Peptide inker
<221> NAME/KEY: VARIANT
<222> LOCATION: (3)...(3)
<223> OTHER INFORMATION: Xaa = D or E
<221> NAME/KEY: VARIANT
<222> LOCATION: (4)...(4)
<223> OTHER INFORMATION: Xaa = D or E
<221> NAME/KEY: VARIANT
<222> LOCATION: (5)...(5)
<223> OTHER INFORMATION: Xaa = G, S, or T
<221> NAME/KEY: VARIANT
<222> LOCATION: (6)...(6)
<223> OTHER INFORMATION: Xaa = G, S, or T, or is absent
<221> NAME/KEY: VARIANT
<222> LOCATION: (7)...(7)
<223> OTHER INFORMATION: Xaa = G, S, or T, or is absent

<400> SEQUENCE: 131

Ala Leu Xaa Xaa Xaa Xaa Xaa
1               5

<210> SEQ ID NO 132
<211> LENGTH: 7
<212> TYPE: PRT
<213> ORGANISM: Artificial Sequence
<220> FEATURE:
<223> OTHER INFORMATION: Peptide inker
<221> NAME/KEY: VARIANT
<222> LOCATION: (3)...(3)
<223> OTHER INFORMATION: Xaa = G, S, or T
<221> NAME/KEY: VARIANT
<222> LOCATION: (4)...(4)
<223> OTHER INFORMATION: Xaa = G, S, or T, or is absent
<221> NAME/KEY: VARIANT
<222> LOCATION: (5)...(5)
<223> OTHER INFORMATION: Xaa = G, S, or T, or is absent
<221> NAME/KEY: VARIANT
<222> LOCATION: (6)...(6)
<223> OTHER INFORMATION: Xaa = D or E
<221> NAME/KEY: VARIANT
<222> LOCATION: (7)...(7)
<223> OTHER INFORMATION: Xaa = D or E

<400> SEQUENCE: 132

Ala Leu Xaa Xaa Xaa Xaa Xaa
1               5

<210> SEQ ID NO 133
<211> LENGTH: 7
<212> TYPE: PRT
<213> ORGANISM: Artificial Sequence
<220> FEATURE:
<223> OTHER INFORMATION: Peptide inker
<221> NAME/KEY: VARIANT
<222> LOCATION: (1)...(1)
<223> OTHER INFORMATION: Xaa = G, S, or T
<221> NAME/KEY: VARIANT
<222> LOCATION: (2)...(2)
<223> OTHER INFORMATION: Xaa = G, S, or T
<221> NAME/KEY: VARIANT
<222> LOCATION: (3)...(3)
<223> OTHER INFORMATION: Xaa = G, S, or T
```

```
<221> NAME/KEY: VARIANT
<222> LOCATION: (4)...(4)
<223> OTHER INFORMATION: Xaa = G, S, or T
<221> NAME/KEY: VARIANT
<222> LOCATION: (5)...(5)
<223> OTHER INFORMATION: Xaa = G, S, or T, or is absent
<221> NAME/KEY: VARIANT
<222> LOCATION: (6)...(6)
<223> OTHER INFORMATION: Xaa = G, S, or T, or is absent
<221> NAME/KEY: VARIANT
<222> LOCATION: (7)...(7)
<223> OTHER INFORMATION: Xaa = G, S, or T, or is absent

<400> SEQUENCE: 133

Xaa Xaa Xaa Xaa Xaa Xaa Xaa
 1               5

<210> SEQ ID NO 134
<211> LENGTH: 7
<212> TYPE: PRT
<213> ORGANISM: Artificial Sequence
<220> FEATURE:
<223> OTHER INFORMATION: Peptide inker
<221> NAME/KEY: VARIANT
<222> LOCATION: (1)...(1)
<223> OTHER INFORMATION: Xaa = G, S, or T
<221> NAME/KEY: VARIANT
<222> LOCATION: (2)...(2)
<223> OTHER INFORMATION: Xaa = G, S, or T
<221> NAME/KEY: VARIANT
<222> LOCATION: (3)...(3)
<223> OTHER INFORMATION: Xaa = G, S, or T, or is absent
<221> NAME/KEY: VARIANT
<222> LOCATION: (4)...(4)
<223> OTHER INFORMATION: Xaa = G, S, or T, or is absent
<221> NAME/KEY: VARIANT
<222> LOCATION: (5)...(5)
<223> OTHER INFORMATION: Xaa = G, S, or T, or is absent
<221> NAME/KEY: VARIANT
<222> LOCATION: (6)...(6)
<223> OTHER INFORMATION: Xaa = D or E
<221> NAME/KEY: VARIANT
<222> LOCATION: (7)...(7)
<223> OTHER INFORMATION: Xaa = D or E

<400> SEQUENCE: 134

Xaa Xaa Xaa Xaa Xaa Xaa Xaa
 1               5

<210> SEQ ID NO 135
<211> LENGTH: 7
<212> TYPE: PRT
<213> ORGANISM: Artificial Sequence
<220> FEATURE:
<223> OTHER INFORMATION: Peptide inker
<221> NAME/KEY: VARIANT
<222> LOCATION: (1)...(1)
<223> OTHER INFORMATION: Xaa = G, S, or T
<221> NAME/KEY: VARIANT
<222> LOCATION: (2)...(2)
<223> OTHER INFORMATION: Xaa = G, S, or T
<221> NAME/KEY: VARIANT
<222> LOCATION: (3)...(3)
<223> OTHER INFORMATION: Xaa = G, S, or T
<221> NAME/KEY: VARIANT
<222> LOCATION: (4)...(4)
<223> OTHER INFORMATION: Xaa = G, S, or T
<221> NAME/KEY: VARIANT
<222> LOCATION: (5)...(5)
<223> OTHER INFORMATION: Xaa = G, S, or T
<221> NAME/KEY: VARIANT
<222> LOCATION: (6)...(6)
<223> OTHER INFORMATION: Xaa = G, S, or T, or is absent
```

```
<221> NAME/KEY: VARIANT
<222> LOCATION: (7)...(7)
<223> OTHER INFORMATION: Xaa = G, S, or T, or is absent

<400> SEQUENCE: 135

Xaa Xaa Xaa Xaa Xaa Xaa Xaa
 1               5

<210> SEQ ID NO 136
<211> LENGTH: 7
<212> TYPE: PRT
<213> ORGANISM: Artificial Sequence
<220> FEATURE:
<223> OTHER INFORMATION: Peptide inker
<221> NAME/KEY: VARIANT
<222> LOCATION: (3)...(3)
<223> OTHER INFORMATION: Xaa = D or E
<221> NAME/KEY: VARIANT
<222> LOCATION: (4)...(4)
<223> OTHER INFORMATION: Xaa = D or E
<221> NAME/KEY: VARIANT
<222> LOCATION: (5)...(5)
<223> OTHER INFORMATION: Xaa = G, S, or T
<221> NAME/KEY: VARIANT
<222> LOCATION: (6)...(6)
<223> OTHER INFORMATION: Xaa = G, S, or T, or is absent

<400> SEQUENCE: 136

Ala Leu Xaa Xaa Xaa Xaa Cys
 1               5

<210> SEQ ID NO 137
<211> LENGTH: 7
<212> TYPE: PRT
<213> ORGANISM: Artificial Sequence
<220> FEATURE:
<223> OTHER INFORMATION: Peptide inker
<221> NAME/KEY: VARIANT
<222> LOCATION: (1)...(1)
<223> OTHER INFORMATION: Xaa = G, S, or T
<221> NAME/KEY: VARIANT
<222> LOCATION: (2)...(2)
<223> OTHER INFORMATION: Xaa = G, S, or T
<221> NAME/KEY: VARIANT
<222> LOCATION: (3)...(3)
<223> OTHER INFORMATION: Xaa = G, S, or T
<221> NAME/KEY: VARIANT
<222> LOCATION: (4)...(4)
<223> OTHER INFORMATION: Xaa = G, S, or T, or is absent
<221> NAME/KEY: VARIANT
<222> LOCATION: (5)...(5)
<223> OTHER INFORMATION: Xaa = G, S, or T, or is absent
<221> NAME/KEY: VARIANT
<222> LOCATION: (6)...(6)
<223> OTHER INFORMATION: Xaa = G, S, or T, or is absent

<400> SEQUENCE: 137

Xaa Xaa Xaa Xaa Xaa Xaa Cys
 1               5

<210> SEQ ID NO 138
<211> LENGTH: 7
<212> TYPE: PRT
<213> ORGANISM: Artificial Sequence
<220> FEATURE:
<223> OTHER INFORMATION: Peptide inker
<221> NAME/KEY: VARIANT
<222> LOCATION: (1)...(1)
<223> OTHER INFORMATION: Xaa = G, S, or T
<221> NAME/KEY: VARIANT
<222> LOCATION: (2)...(2)
<223> OTHER INFORMATION: Xaa = G, S, or T, or is absent
```

```
<221> NAME/KEY: VARIANT
<222> LOCATION: (3)...(3)
<223> OTHER INFORMATION: Xaa = G, S, or T, or is absent
<221> NAME/KEY: VARIANT
<222> LOCATION: (4)...(4)
<223> OTHER INFORMATION: Xaa = G, S, or T, or is absent
<221> NAME/KEY: VARIANT
<222> LOCATION: (5)...(5)
<223> OTHER INFORMATION: Xaa = D or E
<221> NAME/KEY: VARIANT
<222> LOCATION: (6)...(6)
<223> OTHER INFORMATION: Xaa = D or E

<400> SEQUENCE: 138

Xaa Xaa Xaa Xaa Xaa Xaa Cys
 1               5

<210> SEQ ID NO 139
<211> LENGTH: 7
<212> TYPE: PRT
<213> ORGANISM: Artificial Sequence
<220> FEATURE:
<223> OTHER INFORMATION: Peptide inker
<221> NAME/KEY: VARIANT
<222> LOCATION: (3)...(3)
<223> OTHER INFORMATION: Xaa = G, S, or T
<221> NAME/KEY: VARIANT
<222> LOCATION: (4)...(4)
<223> OTHER INFORMATION: Xaa = G, S, or T, or is absent
<221> NAME/KEY: VARIANT
<222> LOCATION: (5)...(5)
<223> OTHER INFORMATION: Xaa = D or E
<221> NAME/KEY: VARIANT
<222> LOCATION: (6)...(6)
<223> OTHER INFORMATION: Xaa = D or E

<400> SEQUENCE: 139

Ala Leu Xaa Xaa Xaa Xaa Cys
 1               5

<210> SEQ ID NO 140
<211> LENGTH: 17
<212> TYPE: PRT
<213> ORGANISM: Artificial Sequence
<220> FEATURE:
<223> OTHER INFORMATION: C1s catalytic site directed moiety
<221> NAME/KEY: VARIANT
<222> LOCATION: (1)...(1)
<223> OTHER INFORMATION: Xaa = G, S, or T
<221> NAME/KEY: VARIANT
<222> LOCATION: (3)...(3)
<223> OTHER INFORMATION: Xaa = G, S, or T
<221> NAME/KEY: VARIANT
<222> LOCATION: (4)...(4)
<223> OTHER INFORMATION: Xaa = G, S, or T
<221> NAME/KEY: VARIANT
<222> LOCATION: (5)...(5)
<223> OTHER INFORMATION: Xaa = G, S, or T
<221> NAME/KEY: VARIANT
<222> LOCATION: (6)...(6)
<223> OTHER INFORMATION: Xaa = G, S, or T
<221> NAME/KEY: VARIANT
<222> LOCATION: (7)...(7)
<223> OTHER INFORMATION: Xaa = G, S, or T
<221> NAME/KEY: VARIANT
<222> LOCATION: (8)...(8)
<223> OTHER INFORMATION: Xaa = G, S, or T
<221> NAME/KEY: VARIANT
<222> LOCATION: (9)...(9)
<223> OTHER INFORMATION: Xaa = G, S, or T
<221> NAME/KEY: VARIANT
<222> LOCATION: (10)...(10)
<223> OTHER INFORMATION: Xaa = G, S, or T
```

-continued

```
<221> NAME/KEY: VARIANT
<222> LOCATION: (11)...(11)
<223> OTHER INFORMATION: Xaa = G, S, or T, or is absent
<221> NAME/KEY: VARIANT
<222> LOCATION: (12)...(12)
<223> OTHER INFORMATION: Xaa = G, S, or T, or is absent
<221> NAME/KEY: VARIANT
<222> LOCATION: (13)...(13)
<223> OTHER INFORMATION: Xaa = G, S, or T, or is absent
<221> NAME/KEY: VARIANT
<222> LOCATION: (14)...(14)
<223> OTHER INFORMATION: Xaa = G, S, or T, or is absent

<400> SEQUENCE: 140

Xaa Cys Xaa Xaa Xaa Xaa Xaa Xaa Xaa Xaa Xaa Xaa Xaa Xaa Leu Gln
 1               5                  10                  15

Arg
 20
```